US012708620B2

(12) United States Patent
Heyerick et al.

(10) Patent No.: US 12,708,620 B2
(45) Date of Patent: Aug. 18, 2026

(54) PRODRUGS AND MEDICAL USES THEREOF

(71) Applicant: CONVERT PHARMACEUTICALS S.A., Liege (BE)

(72) Inventors: Arne Heyerick, Liege (BE); Sofie Deschoemaeker, Liege (BE); Sophie Thiolloy, Liege (BE); Dominique Tersago, Liege (BE); Philippe Lambin, Liege (BE)

(73) Assignee: Convert Pharmaceuticals S.A., Liege (BE)

( * ) Notice: Subject to any disclaimer, the term of this patent is extended or adjusted under 35 U.S.C. 154(b) by 898 days.

(21) Appl. No.: 17/058,632

(22) PCT Filed: May 29, 2019

(86) PCT No.: PCT/EP2019/064112

§ 371 (c)(1), (2) Date: Nov. 24, 2020

(87) PCT Pub. No.: WO2019/229195

PCT Pub. Date: Dec. 5, 2019

(65) Prior Publication Data

US 2021/0205299 A1 Jul. 8, 2021

(30) Foreign Application Priority Data

May 30, 2018 (EP) .................................... 18175264

(51) Int. Cl.
*A61K 31/495* (2006.01)
*A61K 45/06* (2006.01)
*A61P 35/04* (2006.01)

(52) U.S. Cl.
CPC ............ *A61K 31/495* (2013.01); *A61K 45/06* (2013.01); *A61P 35/04* (2018.01)

(58) Field of Classification Search
CPC .... A61K 31/495; A61K 45/06; A61K 31/277; A61K 31/166; A61P 35/04; A61P 35/00
See application file for complete search history.

(56) References Cited

U.S. PATENT DOCUMENTS

2011/0190310 A1 8/2011 Lewis
2018/0148463 A1 5/2018 Smaill

FOREIGN PATENT DOCUMENTS

WO 2010044685 4/2010
WO 2014031012 2/2014
WO WO-2014031012 A * 2/2014 .............. A61P 31/00
WO 2019125184 6/2019

OTHER PUBLICATIONS

Menon, Cancers , 2016, 8, 106 (Year: 2016).*
Torgovnick, Front. Genet. 2015, 6:157 (Year: 2015).*
NCI, National Cancer Institute, Metastatic Cancer, dated 2016, url= https://www.cancer.gov/types/metastatic-cancer, accessed Feb. 21, 2025 (Year: 2016).*
Schaake-Koning, The New England Journal of Medicine, vol. 325, No. 8, 1992 (Year: 1992).*
Notice of Reasons for Refusal issued in Japnese Application No. 2021-517520 drafted May 17, 2023.
BMC Cancer, "PR-104 a bioreductive pre-prodrug combined with gemcitabine or docetaxel in a phase lb study of patients with advanced solid tumours", Mckeage, Oct. 25, 2012, vol. 12, No. 496, p. 1-10.
International Search Report, issued in PCT/EP2019/064112, mailed Dec. 12, 2019.
Written Opinion, issued in PCT/EP2019/064112; mailed Dec. 12, 2019.
Chinese Office Communication issued in Chinese Application 201980036567.5 issued Nov. 1, 2023.

* cited by examiner

*Primary Examiner* — Susanna Moore
*Assistant Examiner* — Luisalberto Gonzalez
(74) *Attorney, Agent, or Firm* — Ferguson Case Orr Paterson LLP

(57) ABSTRACT

The invention relates to nitrogen mustards bearing substituted piperazine carboxamide and their corresponding pharmaceutically acceptable salts as cytotoxic agents that target tumours and methods of use thereof, alone or in combination with other cancer treatments.

18 Claims, 7 Drawing Sheets

A)

piperazine-*d8*

*3-d8-Boc*

PIP-*d8*

4

5

*6-d8*

B)

Cpd.11Ms

Cpd.11c

C)

Cpd.11Ms-d8

Cpd.11c-d8

D)

Cpd.11Ms

Cpd.11d

E)

Cpd.11Ms-d8

Cpd.11d-d8

PRODRUGS AND MEDICAL USES THEREOF

TECHNICAL FIELD OF THE INVENTION

The invention relates to nitrogen mustards bearing substituted piperazine carboxamide and their corresponding pharmaceutically acceptable salts as cytotoxic agents that target tumours and methods of use thereof, alone or in combination with other cancer treatments.

BACKGROUND OF THE INVENTION

The use of tumour-selective prodrugs (that is, therapeutically inactive compounds that can be selectively converted to therapeutically active compounds by cellular metabolism and/or within the tumor microenvironment) is an approach that has been exploited in cancer therapy for targeting cells presenting cancer-specific features such as hypoxia. In particular, hypoxia-activated prodrugs (HAPs) that become cytotoxic agents only into low-oxygen tumour compartments, are indicated as promising antineoplastic agents in particular in case of adverse prognosis, drug combinations, and/or resistance to standard-of-care treatments (Hunter F et al., 2016; Mistry I N et al., 2017; Phillips R, 2016; Silva V L and Al-Jamal W T, 2017).

Most tumours, in particular solid ones that are highly aggressive and/or drug resistant, present more or less extensive hypoxic regions resulting from the development of an inefficient blood vessel network. HAPs with alkylating groups, such as nitrogen mustards, are designed to selectively eliminate cancer cells in hypoxic tumours by inducing DNA damage within the hypoxic regions, extending their cytotoxic activity beyond such area as a result of redistribution upon activation (bystander effect) while having only minimal toxicity in normal tissues.

Among HAPs, such as nitrogen mustards and their chemical derivatives have been tested in preclinical models (WO2009140553; WO2014031012; Baran N and Konopleva M, 2017). However, such compounds have not yet confirmed their clinical efficacy in cancer patients or in cancer animal models, at least as potential broad-spectrum cytotoxic agents and/or therapeutically useful in specific types of tumours. These studies have possibly failed due to an incomplete understanding and evaluation of tumour hypoxia and of the pharmacology of HAPs. Indeed, HAPs therapeutic properties are actually dependent on both their own physico-chemical features and tumour-specific properties that make cancer cells intrinsically sensitive (or not) to a cytotoxic agent. Moreover, such HAPs may present unfavourable pharmaceutical features such as poor aqueous solubility, low maximum tolerated dose, low bystander effect, off-mechanism activation by human aerobic reductases and/or not orally bioavailable.

Thus, it would be valuable and useful to characterize, among the nitrogen mustards, those presenting suitable pharmaceutical and therapeutic properties, at least in specific cancers such as breast cancer, lung cancer, and pancreatic cancer, in general and in particular when these properties apply to specific sub-types of cancers and/or improve standard-of-care treatments.

SUMMARY OF THE INVENTION

The present invention provides, in some aspects, compositions and methods that are useful for the treatment of cancer, including combination therapies and regimens involving anti-cancer drugs and immunotherapies, that involves the use of nitrogen mustards bearing a substituted piperazine carboxamide, in particular symmetrical or unsymmetrical haloalkanesulfonate-bearing mustards (or simply haloalkanesulfonates mustards, as indicated in the text below). In particular the present invention relates to compounds as defined herein below, or a salt, solvate, or stereoisomer thereof, for use in a method of treating breast cancer, pancreatic cancer, or lung cancer, in a patient in need thereof. Otherwise formulated, the present invention relates to a method of treating a patient with breast cancer, pancreatic cancer, or lung cancer, the method comprising administering an effective amount of a compound of the invention, or a salt, solvate, or stereoisomer thereof, to a patient in need thereof.

This method preferably applies in conditions where one or more cancers that are present in a patient (being breast cancer, pancreatic cancer, lung cancer, as well as their metastasis or other type of cancers such as gastrointestinal cancer, prostate cancer, ovarian cancer, brain cancer, head & neck cancer, or soft tissue sarcoma) are characterized by a measurable or otherwise detectable hypoxic region that is sensitive to the administration of haloalkanesulfonates mustards and/or of their metabolites in which one or groups are modified in anoxic or normoxic conditions in vivo, or made available by chemical synthesis. The relevant cancer-specific hypoxic state can be determined prior, during, and after treating the patient by using non-invasive technologies (such as magnetic resonance or radiology) or by technologies requiring the analysis of biological samples obtained from the patients (such as tumor biopsies or blood analysis), in order to associate or predict cancer-specific hypoxic state by means of a specific gene expression criteria within such samples (such as a gene expression signature).

In some aspects, the symmetrical or unsymmetrical haloalkanesulfonates mustards, and a salt, solvate, or stereoisomer thereof that are used in composition and methods for treating cancer according to the invention, have the structure defined by Formula (I):

(I)

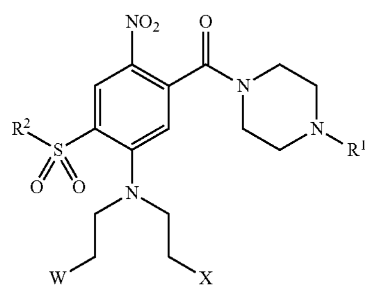

and a salt, solvate, or stereoisomer thereof, wherein:

W represents Cl, Br, I, $OSO_2R^3$;

X represents Cl, Br, I, $OSO_2R^3$; and

Each of $R^1$, $R^2$, and $R^3$ independently represents a H or $C_{1-6}$ alkyl.

Preferred compounds of Formula (I) that are used in methods and compositions in accordance to the invention, are those wherein at least one (but preferably all of) $R^1$, $R^2$, and $R^3$ represents a $C_{1-6}$ alkyl, and more preferably wherein W is Br or I, and X is $OSO_2Me$ or Br. Moreover, $R^2$ is preferably methyl or ethyl, and $R^1$ is methyl, ethyl, propyl, or iso-propyl. For example, a preferred compound of Formula (I) is 2-((2-bromoethyl) (5-(4-ethylpiperazine-1-carbonyl)-2-(methylsulfonyl)-4-nitrophenyl)amino)ethyl methanesulfonate (Compound 11, or Cpd.11). The preferred compounds of Formula (I) can be defined and grouped as unsymmetrical or symmetrical haloalkanesulfonate-bearing mustards presenting specific combinations in each of $R^1$ and $R^2$.

Preferably a compound of Formula (I) is used in methods and compositions in accordance to the invention in the form of a pharmaceutically acceptable salt, such as a methanesulfonate salt. For example, a preferred pharmaceutically acceptable salt of a compound of Formula (I) is methanesulfonate salt of 2-((2-bromoethyl) (5-(4-ethylpiperazine-1-carbonyl)-2-(methylsulfonyl)-4-nitrophenyl)amino)ethyl methanesulfonate (Compound 11 Ms, or Cpd.11 Ms).

The compounds of Formula (I) may be biologically active and/or provided under the alternative Formula (II):

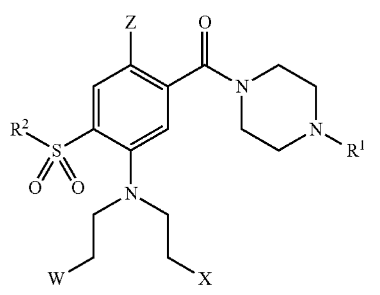

(II)

Wherein W, X, $R^1$, $R^2$, and $R^3$ have the same general and preferred definitions of Formula (I) and Z can be NHOH (hydroxylamine) or $NH_2$ (amine). A preferred compound of Formula (I) is a metabolite or a derivative of 2-((2-bromoethyl) (5-(4-ethylpiperazine-1-carbonyl)-2-(methylsulfonyl)-4-nitrophenyl)amino)ethyl methanesulfonate (Compound 11) wherein Z is NHOH (in Compound 11c, or Cpd.11c) or $NH_2$ (in Compound 11d, or Cpd.11d). The metabolization of such preferred compounds may lead to compounds where either W or X is Cl, (or both W and X are Cl) and that may react with specific cellular components, such as nucleic acids and in particular chromosomal DNA, thus forming cytotoxic DNA adducts.

In general, a compound of Formula (I) (or Formula (II)) exerts hypoxia-dependent cytotoxicity in human cancer cells, including cells present in hypoxic regions of cancers. This cytotoxicity can be evaluated in cancer cells that are found, isolated or selected from breast cancer, lung cancer, pancreatic cancer, gastrointestinal cancer, prostate cancer, ovarian cancer, brain cancer, head and neck cancer, and soft tissue sarcoma. Such cancer cells may be derived from primary cancer cells from biopsies, tumor spheroids, or established cancer cell lines that can be tested in vitro or ex vivo (e.g. as xenograft in murine cancer models). Given the experimental characterization of compounds of Formula (I) (or Formula (II)) that is provided in the present invention, said compounds can be administered to a subject having hypoxic tumor cells, as established using appropriate technologies in vivo or ex vivo, for instance using specific markers, tracers, and/or cancer cells derived from lung, pancreatic, or breast cancer.

The compound of Formula (I) (or Formula (II)) to be used in methods and compositions according to the present invention may be further defined with respect to criteria associated to biological activities determined in hypoxic conditions, compared or not to those observed in normoxic conditions (or independent from the presence of oxygen). For example such criteria may be the hypoxia cytotoxicity ratio (HCR) that can be measured in vitro using tumor biopsies or cancer cell lines (such as in human cancer cells selected from breast cancer cells, lung cancer cells, pancreatic cancer cells, gastrointestinal cancer cells, prostate cancer cells, ovarian cancer cells, brain cancer cells, head and neck cancer cells, and/or soft tissue sarcoma cells, in particular when presenting hypoxic regions, as indicated above) and comprised in a range of values (such as between 2 to 250, 5 and 250, or any intermediate range such as 5 to 150 or 4 to 190).

Preferably, the compounds of Formula (I) (or of Formula (II)) are used in compositions and methods according to the invention for treating, ameliorating, or preventing breast cancer, pancreatic cancer, lung cancer, gastrointestinal cancer, prostate cancer, ovarian cancer, brain cancer, head and neck cancer, or soft tissue sarcoma, in particular when presenting hypoxic regions. Specific subtype or variants of such cancer can be additionally defined by clinically or biologically relevant criteria (such as specific morphology, origin, stage, drug resistance, relapse, previous therapeutic treatments, metastatic properties, epithelial-mesenchymal transition, immunologic escape, cancer recurrence, and/or cancer-specific molecular markers). Sub-types of such cancers that can be treated in accordance to the present invention are small cell lung carcinoma or non-small-cell lung carcinoma (for lung cancer), as triple negative breast neoplasm (for breast cancer (such), or pancreatic adenocarcinoma (for pancreatic cancer), and further ones that are listed in the Detailed Description and in the Examples below.

The subjects that are affected by any of such cancers may have previously been treated (or not) with standard-of-care protocols (such as radiotherapy, chemotherapy, and/or immunotherapy) prior to treatment using the compounds of Formula (I) (or of Formula (II)) and related compositions and methods. Such treatment may be intended to avoid (or prevent) drug resistance (including reduced, or lack of, efficacy of standard-of-care treatments listed above), cancer recurrence or relapse, immunological escape (resistance of cancer cells to immune rejection), or metastasis, and may be evaluated with respect to cancer cell growth, tumor regression, or other clinically relevant criteria that allow defining appropriate further treatment or clinical protocol, still including (or not) a compound of Formula (I) (or of Formula (II)).

The pharmaceutical compositions and methods that involve the use of a compound of Formula (I) (or of Formula (II)) or related pharmaceutically acceptable salt can be established by formulating such compound (with or without a pharmaceutically acceptable excipient, adjuvant, carrier, buffer, diluent, or stabilizer), in particular for parenteral administration (and more preferably for subcutaneous or intravenous administration), intratumoral administration, trans-arterial embolization administration, or oral administration. Such compositions can be administered to a subject to be treated for a cancer (in particular, for lung, pancreatic, or breast cancer) in a therapeutically effective amount, preferably at a dose comprised between 40 to 4000 $mg/m^2$ or higher, up to between 4000 to 10,000 $mg/m^2$ (or alternatively defined as 1 to 100 mg/Kg or higher, up to between 100 mg/Kg and 250 mg/Kg). The compound or the pharmaceutical composition can be administered one day per month, or at a frequency of every day for 2, 3, 4, or 5 consecutive (or non-consecutive) days per month or per each cycle (over 2, 3, or four weeks). This regimen can be pursued for one or more months, for instance up to 12 months, involving or not the further administration of other anti-tumor therapies and in particular standard-of-care protocols (such as radiotherapy, chemotherapy, and/or immunotherapy).

A further object of the invention is the use of a compound of Formula (I) (or of Formula (II)) or related pharmaceutically acceptable salt, compositions, or formulations in combination with a another therapeutic agent or therapy, in particular a therapeutic agent or therapy that is useful for treating breast cancer, lung cancer, pancreatic cancer, gastrointestinal cancer, prostate cancer, ovarian cancer, brain cancer, head and neck cancer, and/or soft tissue sarcoma (as well as any specific variant of subtype of such cancers). These agents and therapies are selected from radiotherapy, chemotherapy, immunotherapy, and/or any other approach that involve the use of an agent that modulates one or more biological targets relevant for cancer, in particular breast cancer, lung cancer, pancreatic cancer or other type or sub-types of cancer listed above, in particular when presenting hypoxic regions. These combinations may be particularly useful for improving cancer treatment (such as tumor regression, extended survival, reduction or absence of metastasis, etc.) and/or improving the effect of the other agent or therapy (such as reduced dosages, limitation of side effects, broader therapeutic window, reduction of drug-specific resistance, etc.). These combinations can be provided in compositions and regimens for simultaneous, alternate, or sequential administration of a compound of Formula (I) (or of Formula (II)) with such other agent or therapy.

Further embodiments of the invention related to use of the compounds of Formula (I) or Formula (II) in composition and methods for treating cancer (in general or specific sub-types of cancer), preferred compounds of Formula (I) or Formula (II), the preparation of such compounds and related formulations, specific dosages and regimens, and specific combinations with other agents or therapies, are provided in the Detailed Description and in the Examples below.

DETAILED DESCRIPTION OF THE INVENTION

Figure 1:
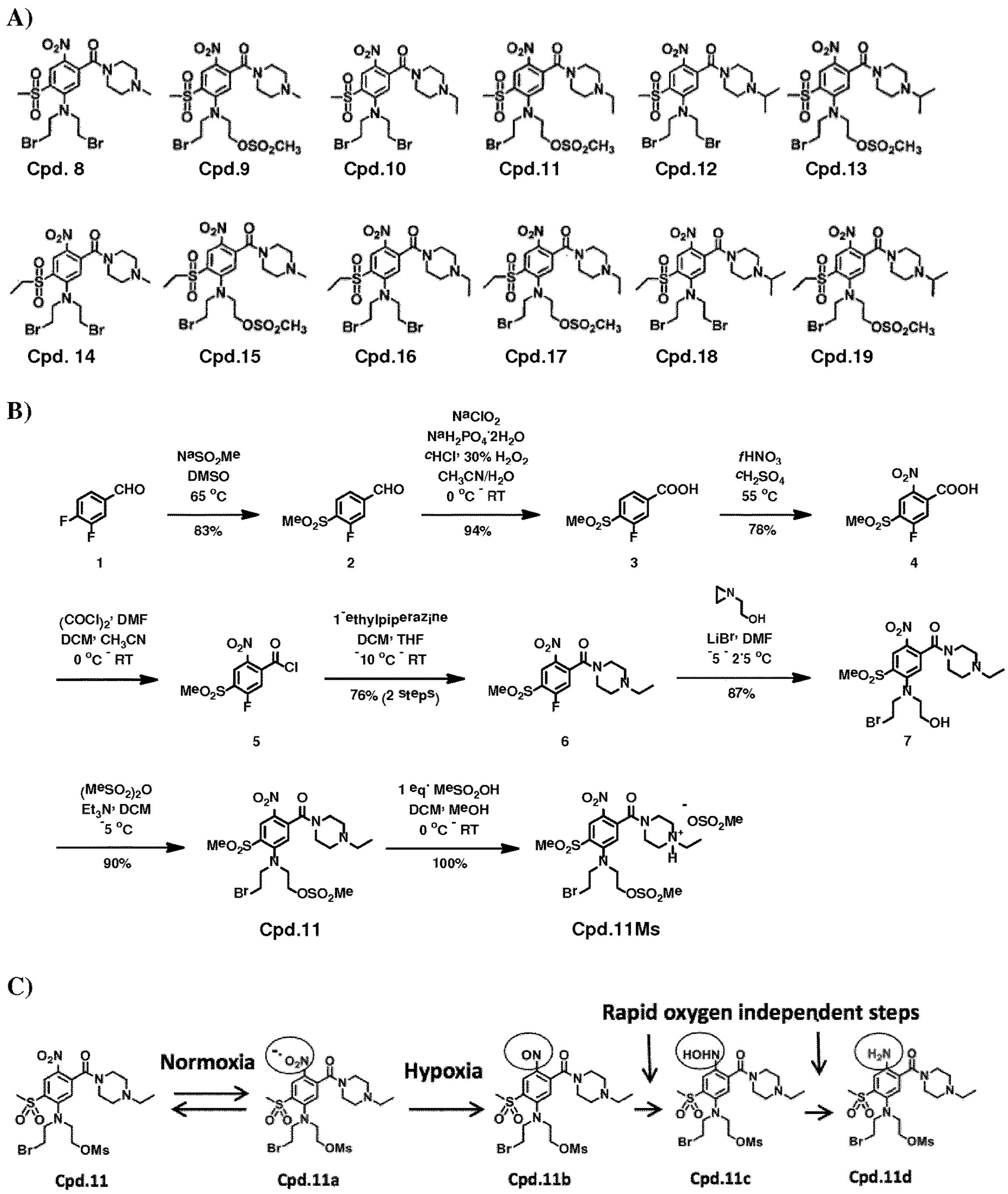
FIG. 1: symmetrical or unsymmetrical haloalkanesulfonate mustards of formula I that can be used according to the invention. The structure of Cpd.8-Cpd.19, specific symmetric or unsymmetric haloalkanesulfonate-bearing mustards of formula (I) is provided (A). The synthesis process of the reference unsymmetrical haloalkanesulfonate mustard of formula I named Cpd.11 Ms (B) includes initial steps that are described in WO2014031012, starting from 3,4-difluorobenzaldehyde (compound 1) that is treated with sodium sulfinate, obtaining the corresponding alkylsulfone (compound 2), followed by oxidation leading to the corresponding benzoic acid (compound 3). Classical nitration gives compound 4 which is converted into the corresponding acid chloride (compound 5), and further reacted with 1-ethylpiperazine to give intermediate amide (compound 6). Reaction with lithium bromide and aziridine ethanol gives compound 7 which is then functionalized with methanesulfonic anhydride to give 2-((2-bromoethyl) (5-(4-ethylpiperazine-1-carbonyl)-2-(methylsulfonyl)-4-nitrophenyl) amino)ethyl methanesulfonate, which is identified as compound 11 (Cpd.11). Salt formation with methanesulfonic acid gives Compound 11 Ms (Cpd.11 Ms; 4-(5-((2-bromoethyl) (2-((methylsulfonyl)oxy)ethyl)amino)-4-(methylsulfonyl)-2-nitrobenzoyl)-1-ethylpiperazin-1-ium methanesulfonate). The haloalkanesulfonate mustards of Formula (I) can be metabolized in vivo by human enzymes into a series of cytotoxic compounds, as exemplified with Compound 11, that is modified into the intermediate Compound 11a (Cpd.11a) and then into Compound 11b (Cpd.11b) in hypoxic conditions present within the tumour environment and then into the cytotoxic Compounds 11c (Cpd.11c) and 11d (Cpd.11d) by an oxygen-independent mechanism (C). These metabolites may be further modified in vivo due to presence of physiological salts so that the Bromine and/or OMs group is substituted by a Chlorine atom, generating mono- or dichloride derivatives.

Preferred compounds among those defined under Formula (I) or Formula (II) to be used in methods and compositions according to the present invention are those presenting specific combinations of substituents in the positions defined as W, X, $R^1$, $R^2$, $R^3$, and Z, and related salt, solvate, or stereoisomer thereof. These compounds are defined therapeutically active in selected types of cancer that, as shown in Examples using relevant cell-based animal models, are particularly sensitive and regress when exposed to an exemplary compound of Formula (I). These evidences support the use of a compound of the invention, or a salt, solvate, or stereoisomer thereof, in the treatment of patients with breast cancer, pancreatic cancer, lung cancer, gastrointestinal cancer, prostate cancer, ovarian cancer, brain cancer, head and neck cancer, or soft tissue sarcoma, and specific subtypes that are defined at the clinical and/or molecular level, in particular with respect to the presence of hypoxic regions.

These methods of treatment according to the present invention comprise the administration of an effective amount of a compound of Formula (I) or Formula (II) and may further involve the prior, simultaneous, alternate, sequential administration of another therapeutically active compound, in particular for treating cancer, including radiotherapy, chemotherapy, immunotherapy, or any therapy involving the administration of a compound that modulates a cancer-related target. The combination therapies may involve therapies or agents that may provide a further, complementary therapeutic effect in particular in breast, lung, and/or pancreatic cancer that is independent from hypoxia.

As used herein, the terms "treat," "treating", or "treatment" include alleviating, abating or ameliorating at least one symptom of a disease or condition, preventing additional symptoms, preventing progression of the condition, inhibiting the disease or condition, e.g., arresting the development of the disease or condition, relieving the disease or condition, causing regression of the disease or condition, relieving a condition caused by the disease or condition, or stopping the symptoms of the disease or condition. In one embodiment, treatment is prophylactic treatment. In one embodiment, treatment refers to therapeutic treatment. In either of said embodiments, the treatment may provide an improvement of a disease or condition alone or in combination with a standard-of-care treatment, according to any preferred, clinically compliant dosage or regimen.

Among the compounds of Formula (I) for the use according to the present invention, $R^1$ represents, the preferred compounds have $C_{1-6}$ alkyl as $R^1$ and/or $R^2$. Among these preferred compounds of Formula (I) for the use according to the present invention, those provided as unsymmetrical haloalkanesulfonates mustards have $C_{1-6}$ alkyl as $R^3$.

As used herein, the "$C_{1-6}$ alkyl" defining $R^1$, $R^2$, and $R^3$ groups refers to an aliphatic hydrocarbon group comprising from 1 to 6 carbon atoms. Reference to $C_{1-6}$ alkyl includes "saturated $C_{1-6}$alkyl" and/or "unsaturated $C_{1-6}$alkyl". The definition of $C_{1-6}$ alkyl group, whether saturated or unsaturated, includes branched, straight chain, or cyclic groups. By way of example only, $C_{1-6}$ alkyl includes methyl, ethyl, propyl, iso-propyl, n-butyl, iso-butyl, sec-butyl, t-butyl, pentyl, isopentyl, neo-pentyl, hexyl, ethenyl, propenyl, butenyl, cyclopropyl, cyclobutyl, cyclopentyl, and cyclohexyl.

Preferred compounds among those defined under Formula (I) that are used in composition and methods for treating cancer according to the invention, can be defined and grouped as presenting identical $C_{1-6}$ alkyl in each of $R^1$ and $R^2$, wherein $R^2$ is preferably methyl or ethyl, and $R^1$ is methyl, ethyl, propyl, or iso-propyl. These preferred compounds can be provided as either symmetrical or unsymmetrical (haloalkanesulfonate-bearing) haloalkanesulfonates mustards. In the former case, both W and X represent Cl, Br, or I, (and preferably both W and X being Bromine). In the latter case, W represents Cl, Br, or I, (and preferably W being Bromine), $R^3$ represents a $C_{1-6}$ alkyl (and preferably represents a methyl), and $R^3$ represents a $C_{1-6}$ alkyl (and preferably represents a methyl).

According to this preferred embodiment, the preferred compounds according to Formula (I) are selected from unsymmetrical or symmetrical haloalkanesulfonate-bearing mustards presenting the following combinations in each of $R^1$ and $R^2$ (see FIG. 1A):

(a) when both and $R^2$ are methyl, the compound is 5-(bis $R^1$ (2-bromoethyl)amino)-4-(methylsulfonyl)-2-nitrophenyl) (4-methylpiperazin-1-yl) methanone (compound 8) or 2-((2-bromoethyl) (5-(4-methylpiperazine-1-carbonyl)-2-(methylsulfonyl)-4-nitrophenyl)amino) ethyl methanesulfonate (compound 9);

(b) when $R^1$ is ethyl and $R^2$ is methyl, the compound is 5-(bis (2 bromoethyl)amino)-4-(methylsulfonyl)-2-nitrophenyl) (4-ethylpiperazin-1-yl) methanone (compound 10) or 2-((2-bromoethyl) (5-(4-ethylpiperazine-1-carbonyl)-2-(methylsulfonyl)-4-nitrophenyl)amino) ethyl methanesulfonate (compound 11);

(c) when $R^1$ is isopropyl and $R^2$ is methyl, the compound is (5-(bis(2-bromoethyl)amino)-4-(methylsulfonyl)-(2-nitrophenyl) (4-isopropylpiperazin-1-yl) methanone (compound 12), or 2-((2-bromoethyl) (5-(4-isopropylpiperazine-1-carbonyl)-2-(methylsulfonyl)-4-nitrophenyl)amino)ethyl methanesulfonate (compound 13);

(d) when $R^1$ is methyl and $R^2$ is ethyl, the compound is 5-(bis (2-bromoethyl)amino)-4-(ethylsulfonyl) (2-nitrophenyl) (4-methylpiperazin-1-yl) methanone (compound 14), or 2-((2-bromoethyl) (2-(ethylsulfonyl)-5-(4-methylpiperazine-1-carbonyl)-4-nitrophenyl) amino)ethyl methanesulfonate (compound 15);

(e) when both $R^1$ and $R^2$ are ethyl, the compound is 5-(bis (2-bromoethyl)amino)-4-(ethylsulfonyl)-(2-nitrophenyl) (4-ethylpiperazin-1-yl) methanone (compound 16), or 2-((2-bromoethyl) (5-(4-ethylpiperazine-1-carbonyl)-2-(ethylsulfonyl)-4-nitrophenyl)amino)ethyl methanesulfonate (compound 17); or (f) when $R^1$ is isopropyl and $R^2$ is ethyl, the compound is 5-(bis (2 bromoethyl)amino) 4 (ethylsulfonyl)-(2 nitrophenyl) (4-isopropylpiperazin-1-yl) methanone (compound 18), or 2-((2-bromoethyl) (2-(ethylsulfonyl)-5-(4-isopropylpiperazine-1-carbonyl)-4-nitrophenyl) amino)ethyl methanesulfonate (compound 19).

Alternatively, preferred compounds among those defined under Formula (I) that are used in composition and methods for treating cancer according to the invention, can be defined and grouped as being either symmetrical or unsymmetrical haloalkanesulfonates mustards with alternative $R^1$ and $R^2$ substituents. In the former case, both W and X represents Cl, Br, or I, (and preferably both W and X being Bromine), and preferably at least one $R^1$ and $R^2$ (but more preferably both $R^1$ and $R^2$) represents a $C_{1-6}$ alkyl.

In a further preferred embodiment for symmetrical haloalkanesulfonates mustards, $R^2$ is preferably methyl or ethyl, and $R^1$ is methyl, ethyl, propyl, or iso-propyl. In the latter case, W represents Cl, Br, or I, (and preferably W being Bromine), $R^3$ represents a $C_{1-6}$ alkyl (and preferably represents a methyl), preferably at least one $R^1$ and $R^2$ (but more preferably both $R^1$ and $R^2$) represents a $C_{1-6}$ alkyl. In a preferred embodiment for unsymmetrical haloalkanesulfonates mustards, $R^2$ is preferably methyl or ethyl, and $R^1$ is methyl, ethyl, propyl, or iso-propyl. According to this embodiment, most preferred compounds according to Formula (I) are selected from:

(a) 5-(bis(2-bromoethyl)amino)-4-(methylsulfonyl)-2-nitrophenyl) (4-methylpiperazin-1-yl) methanone (compound 8), 5-(bis(2-bromoethyl) amino)-4-(methylsulfonyl)-2-nitrophenyl) (4-ethylpiperazin-1-yl) methanone (compound 10), 5-(bis(2-bromoethyl) amino)-4-(methylsulfonyl)-(2-nitrophenyl) (4-isopropylpiperazin-1-yl) methanone (compound 12), 5-(bis (2-bromoethyl) amino)-4-(ethylsulfonyl)-(2-nitrophenyl) (4-methylpiperazin-1-yl) methanone (compound 14), 5-(bis(2-bromoethyl)amino)-4-(ethylsulfonyl)-(2-nitrophenyl) (4-ethylpiperazin-1-yl) methanone (compound 16), and 5-(bis(2-bromoethyl) amino)-4-(ethylsulfonyl)-(2-nitrophenyl) (4-isopropylpiperazin-1-yl) methanone (compound 18); or (b) 2-((2-bromoethyl) (5-(4-methylpiperazine-1-carbonyl)-2-(methylsulfonyl)-4-nitrophenyl)amino)ethyl methanesulfonate (compound 9), 2-((2-bromoethyl) (5-(4-ethylpiperazine-1-carbonyl)-2-(methylsulfonyl)-4-nitrophenyl)amino)ethyl methanesulfonate (compound 11), 2-((2-bromoethyl) (5-(4-isopropylpiperazine-1-carbonyl)-2-(methylsulfonyl)-4-nitrophenyl)amino) ethyl methanesulfonate (compound 13), 2-((2-bromoethyl) (2-(ethylsulfonyl)-5-(4-methylpiperazine-1-carbonyl)-4-nitrophenyl)amino)ethyl methanesulfonate (compound 15), 2-((2-bromoethyl) (5-(4-ethylpiperazine-1-carbonyl)-2-(ethylsulfonyl)-4-nitrophenyl)amino)ethyl methanesulfonate (compound 17), and 2-((2-bromoethyl) (2-(ethylsulfonyl)-5-(4-isopropylpiperazine-1-carbonyl)-4-nitrophenyl)amino) ethyl methanesulfonate (compound 19).

Independently from either definition of the preferred compounds according to Formula (I) that are defined above (that is as either unsymmetrical or unsymmetrical haloalkanesulfonates mustards with combinations of substituents in $R^1$ and $R^2$, or as haloalkanesulfonates mustards with combinations of $R^1$ and $R^2$ that are either unsymmetrical or unsymmetrical due to substituent in X), a preferred compound of Formula (I) that is used in composition and methods for treating cancer (and in particular breast cancer, lung cancer, pancreatic cancer, gastrointestinal cancer, prostate cancer, ovarian cancer, brain cancer, head and neck cancer, or soft tissue sarcoma, in particular when presenting hypoxic regions) according to the invention, is 2-((2-bromoethyl) (5-(4-ethylpiperazine-1-carbonyl)-2-(methylsulfonyl)-4-nitrophenyl)amino) ethyl methanesulfonate (compound 11), and any salt, solvate, or stereoisomer.

Moreover, independently from either definition of the preferred compounds according to Formula (I) that are defined above, these compounds can be provided under the further alternative, corresponding compounds of Formula (II) being the metabolites that result from modification of $—NO_2$ substituent in Formula (I) into alternative nitrogen-based substituent (for example hydroxylamine or amine).

Compounds of Formula (I), or salt, solvate, or stereoisomer thereof, can be provided as prodrugs that are metabolized after their administration in vivo, in particular as compounds of Formula (II). Preferred compounds of Formula (II) are the compounds of Formula (I) wherein Z can be NHOH or NH2 that, as shown for Compound 11 in FIG. 1C, may lead to metabolites after its administration in the form of active metabolite Compound 11c and Compound 11d that are cytotoxic for cancer cells The compounds of Formula (II) may be also provided in accordance to any alternative process for producing derivative compounds of Formula (I), for example starting from an intermediate compounds in the synthesis of compounds of Formula (I).

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes, such as oxidation reactions, or reductions catalyzed by nitroreductases) by which a particular substance is changed by an organism. Thus, enzymes may produce specific structural alterations to a compound. For example, cytochrome P450 catalyzes a variety of oxidative and reductive reactions while uridine diphosphate glucuronyl transferases catalyze the transfer of an activated glucuronic-acid molecule to aromatic alcohols, aliphatic alcohols, carboxylic acids, amines and free sulfhydryl groups. Further information on metabolism may be obtained from Goodman and Gilman's The Pharmacological Basis of Therapeutics (13th Edition, 2017; McGraw-Hill). Metabolites of the compounds disclosed herein can be identified either by administration of compounds to a host (followed by the analysis of tissue samples from the host, being humans or animal models) or by incubating compounds with human or animal cells in cell culture in vitro/ex vivo conditions (followed by the analysis of cell extracts and/or cell culture medium). Both methods are well known in the art. Particular pharmacologically active metabolites according to the present invention are formed by reduction of the nitro moiety of the compounds of Formula (I), thereby generating the active hydroxylamine- and amine-containing metabolites, as identified by Formula (II). Moreover, a chlorine atom can be present in a metabolite of compounds of Formula (I), as alternative W group, X group (or both), after reacting in vivo with physiological salts.

Whenever used hereinafter, the phrase "compounds of Formula (I)", "compounds of Formula (II)", "present compound", or "the present compounds" or similar terms, it is meant to include the compounds of Formula (I) or Formula (II), the salts, solvates, and stereochemically isomeric forms thereof. The compounds of Formula (I) or Formula (II) may have centers of chirality, particularly in respect to $R^1$, $R^2$ or $R^3$ groups when branched, and may exist as stereochemically isomeric forms.

The present invention is also intended to include all isotopes of atoms occurring on the present compounds. Isotopes include those atoms having the same atomic number but different mass numbers. By way of general example and without limitation, isotopes of hydrogen include tritium and deuterium. Isotopes of carbon include C-13 and C-14.

Examples of compounds of Formula (I) or Formula (II) are provided in the Example 1 as deuterated variants in which hydrogen atoms of the piperazine ring are substituted by deuterium (as exemplified with structure and methods of synthesis of Cpd.11-d8, Cpd.11s-d8, and Cpd.11d-d8).

The term "stereochemically isomeric forms" as used herein defines all the possible compounds made up of the same atoms bonded by the same sequence of bonds but having different three-dimensional structures which are not interchangeable, which the compounds of formula (I) may possess. With reference to the instances where (R) or(S) is used to designate the absolute configuration of a chiral atom within a substituent, the designation is done taking into consideration the whole compound and not the substituent in isolation. Unless otherwise mentioned or indicated, the chemical designation of a compound encompasses the mixture of all possible stereo chemically isomeric forms, which said compound might possess. Said mixture may contain all diastereomers and enantiomers of the basic molecular structure of said compound. All stereochemically isomeric forms of the compounds of the present invention both in pure form or mixed with each other are intended to be embraced within the scope of the present invention.

Pure stereoisomeric forms of the compounds of Formula (I) or Formula (II) and intermediates as mentioned herein are defined as isomers substantially free of other enantiomeric or diastereomeric forms of the same basic molecular structure of said compounds or intermediates. In particular, the term "stereoisomerically pure" concerns compounds or intermediates having a stereoisomeric excess of at least 80% (i.e. minimum 80% of one isomer and maximum 20% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms "enantiomerically pure" and "diastereomerically pure" should be understood in a similar way.

Pure stereoisomeric forms of the compounds of Formula (I) or Formula (II) and intermediates as mentioned herein may be obtained by the application of art-known procedures. For instance, enantiomers may be separated from each other by the selective crystallization of their diastereomeric salts with optically active acids or bases. Examples thereof are tartaric acid, dibenzoyltartaric acid, ditoluoyltartaric acid and camphorsulfonic acid.

Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound will be synthesized by stereospecific methods of preparation. These methods will advantageously employ enantiomerically pure starting materials. The diastereomeric racemates of the compounds of Formula (I) or Formula (II) can be obtained separately by conventional methods. Appropriate physical separation methods that may advantageously be employed are, for example, selective crystallization and chromatography, e.g. column chromatography.

Any of the preferred compounds according to Formula (I) that are defined above (that is as either unsymmetrical or unsymmetrical haloalkanesulfonates mustards with combinations of $R^1$, $R^2$, $R^3$, or as haloalkanesulfonates mustards with combinations of $R^1$ and $R^2$ that are either unsymmetrical or unsymmetrical due to $R^3$) are preferably provided in composition and methods for treating cancer according to the invention in the form of a pharmaceutically acceptable salt.

The pharmaceutically acceptable acid and base addition salts as mentioned hereinabove are meant to comprise the therapeutically active non-toxic acid and base addition salt forms that the compounds of Formula (I) or Formula (II) are able to form. The pharmaceutically acceptable acid addition salts can conveniently be obtained by treating the base form with such appropriate inorganic acid (such as hydrochloric acid, hydrobromic acid, sulfuric acid, nitric acid, phosphoric acid and the like) or organic acids such (as acetic acid, methanesulfonic acid, maleic acid, tartaric acid, citric acid and the like) in an anion form. Appropriate anions comprise, for example, acetate, benzenesulfonate, benzoate, bicarbonate, bitartrate, bromide, calcium edetate, camsylate, carbonate, chloride, citrate, dihydrochloride, edetate, estolate, esylate, fumarate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mesylate, methylbromide, methylnitrate, methylsulfate, mucate, nitrate, pantothenate, phosphate/diphosphate, polygalacturonate, salicylate, stearate, subacetate, succinate, sulfate, tannate, tartrate, triethiodide, methansulfonate, tosylate, and the like. Conversely said salt forms can be converted by treatment with an appropriate base into the free base form. More preferably, the salt is methanesulfonate salt. For example, a preferred pharmaceutically acceptable salt of a compound of Formula (I) is methanesulfonate salt of 2-((2-bromoethyl) (5-(4-ethylpiperazine-1-carbonyl)-2-(methylsulfonyl)-4-nitrophenyl)amino)ethyl methanesulfonate (compound 11 Ms).

The compounds of Formula (I) or Formula (II) containing an acidic proton may also be converted into their nontoxic metal or amine addition salt forms by treatment with appropriate organic and inorganic bases in a cation form. Appropriate basic salts comprise those formed with organic cations such as benzathine, chloroprocaine, choline, diethanolamine, ethylenediamine, meglumine, procaine, and the like; and those formed with metallic cations such as aluminum, calcium, lithium, magnesium, potassium, sodium, zinc, and the like. Conversely said salt forms can be converted by treatment with an appropriate acid into the free form. Some of the compounds of Formula (I) or Formula (II) may also exist in their tautomeric form. Such forms, although not explicitly indicated above, are intended to be included within the scope of the present invention.

In some embodiments, compounds of Formula (I) or Formula (II) exist in unsolvated form or in solvated forms with pharmaceutically acceptable solvents such as water, ethanol, alcohols, and the like. The solvated forms of the compounds of Formula (I) or Formula (II) are also considered to be disclosed herein. For therapeutic use, salts of the compounds of Formula (I) or Formula (II) are those wherein the counter-ion is pharmaceutically acceptable, which salts can be referred to as pharmaceutically acceptable acid and base addition salts. Salts of acids and bases that are non-pharmaceutically acceptable may also find use, for example, in the preparation or purification of a pharmaceutically acceptable compound. All salts, whether pharmaceutically acceptable or not, are included within the scope of present invention.

The compounds of Formula (I) of the present invention may be prepared according to the procedures described in WO2014031012, the contents of which are herein incorporated by reference. As shown in FIG. 8 of WO2014031012, reaction of 3,4-difluorobenzaldehyde (100) with sodium alkanesulfinates provides the alkylsulfones (III) which can be oxidised with sodium chlorite in phosphate buffer containing hydrogen peroxide to give the acids (IV). Nitration of these provides the nitroacids (V), which can be reacted directly with diethanolamine to give dials (VI), or first protected to give the tert-butyl esters (VIII), which are subsequently reacted with diethanolamine to give dials (IX). Thionyl chloride mediated chlorination of dials (VI) and subsequent reaction of the resulting acid chloride intermediates with aliphatic amines provides 1-carboxamide dichloro mustards (VII) which can undergo lithium halide mediated halogen exchange in methyl ethyl ketone at reflux to afford compounds of formula (I). Alternately dials (IX) can be converted to their bis-alkanesulfonate esters (X) by reaction with the appropriate alkylsulfonyl chlorides. Tert-butyl ester deprotection of the bis-alkanesulfonate esters (X) with trifluoroacetic acid affords the acids (XI). Reaction of these with oxalyl chloride in the presence of magnesium oxide provides the acid chloride intermediates that can be further reacted with aliphatic amines to give the bis-alkanesulfonate 1-carboxamide derivatives (XII). These can be reacted with excess lithium halide at room temperature in acetone to afford symmetrical mustards of formula I, while reaction with 1 equivalent of lithium halide at room temperature in acetone provides unsymmetrical haloalkanesulfonate mustards of Formula (I).

With respect to symmetrical haloalkanesulfonate mustards of Formula (I), as shown in FIG. 11 of WO2014031012, reaction of bismethanesulfonate ester 109 with oxalyl chloride in the presence of magnesium oxide provided the acid chloride intermediate which was further reacted with 1-methylpiperazine to give the bismethanesulfonate 1-carboxamide 124. Reaction of this with excess lithium bromide at room temperature in acetone gave compound 22. Thionyl chloride mediated chlorination of diol 104 and subsequent reaction of the resulting acid chloride intermediate with 1-ethylpiperazine and 1-iso-propylpiperazine gave the dichloro mustards 131 and 132, respectively. Lithium bromide mediated halogen exchange in methyl ethyl ketone at reflux then gave compounds 23 and 24, respectively. Reaction of bis-methanesulfonate ester 119 with oxalyl chloride in presence of magnesium oxide gave the acid chloride intermediate which was reacted with 1-methylpiperazine, 1-ethylpiperazine and 1-iso-propylpiperazine to give bis-methanesulfonate 1-carboxamides 133, 134 and 135, respectively. Reaction with excess lithium bromide at room temperature in acetone gave compounds 25, 26 and 27, respectively.

Any of the preferred compounds according to Formula (I) that are defined above (that is as either unsymmetrical or unsymmetrical haloalkanesulfonates mustards with combinations of $R^1$, $R^2$, $R^3$, or as haloalkanesulfonates mustards with combinations of $R^1$ and $R^2$ that are either unsymmetrical or unsymmetrical due to group in X) can be also produced by using an alternative process as summarized in FIG. 1B involving the use of aziridine ethanol (or other aziridine alcohol), as such or modified using protecting group chemistry. Common protecting groups are silyl ethers are trimethylsilyl (TMS), triethylsilyl (TES), tert-butyldiphenylsilyl (TBDPS), tert-butyldimethylsilyl (TBS/TBDMS) and triisopropylsilyl (TIPS) that are particularly useful because they can be installed and removed selectively under mild conditions). Any of preferred compounds according to Formula (II) that are defined above may alternatively obtained by modifying the process outlined above, starting from Compound 1, 2, 3, or 4 (FIG. 1B), as such or modified in order to have the desired Z substituent in the final product.

A compound of Formula (I) is intended to exert its therapeutic activity in vivo preferably through its metabolization (into compound of formula (II), for instance) by exerting hypoxia-dependent cytotoxicity (with or without a further by-stander effect) in human cancer cells, preferably cells in hypoxic regions of cancers. This cytotoxicity can be evaluated in cancer cells that are found, isolated or selected from breast cancer, lung cancer, and pancreatic cancer, but also in gastrointestinal cancer, prostate cancer, ovarian cancer, brain cancer, head and neck cancer, and soft tissue sarcoma. Such cancer cells may be derived from primary cancer cells from biopsies, tumor spheroids, or established cancer cell lines that can be tested in vitro or ex vivo (e.g. as xenograft in murine cancer models). In particular, in the presence of pathological hypoxia found in human solid tumors, the reduction to hydroxylamine and amine cytotoxic metabolites may occur. In addition to metabolism by nitroreductases or other enzymes, the compounds of Formula (I) are also metabolised in hypoxic regions that may be found within tumor regions.

"Hypoxic" or "Hypoxia" as referred to herein refers to a concentration of oxygen in tissue that is significantly lower than the normal physiological concentration of oxygen, a condition in which the body or a region of the body is deprived of an adequate oxygen level (resulting from an imbalance between supply and consumption in that region or tissue), in particular when oxygen tensions below approximately 1% (10,000 parts per million oxygen; 7.6 mmHg). Means to evaluate hypoxia in vitro within normal or cancer cells (as adherent cells in monolayers or multilayers, as well as in tumor spheroids) in vivo and in specific tissues or organ are well known from literature. The effects of compounds of Formula (I) (or Formula (II)) can be evaluated as a function of oxygen concentration in such models, in particular evaluating oxygen inhibition of cytotoxicity or hypoxia-dependent induction of γH2AX phosphorylation, repair and response associated to DNA damage, presence of drug-DNA adducts and DNA cross-linking, and/or cell-cycle arrest. At this scope, cell lines presenting defective (or enhanced) hypoxia-dependent activities and/or metabolic activities (such as one or more specific reductases) can be used for identifying how the metabolic activation of compounds of Formula (I) (or Formula (II)) may trigger relevant hypoxia-dependent cytotoxic and significant bystander effect. The compounds of Formula (I) (or Formula (II)) can be evaluated in vivo or in tridimensional models by means of technologies and equipment for imaging or evaluating the metabolite formation in parallel to oxygen and hypoxia in cell and tissue samples, including tracers, radiolabeled or fluorescent probes, or histological analysis (Meng F et al., 2012; Dhingra V K et al., 2015; Papkovsky D B and Dmitriev R I, 2018; Stornetta A et al., 2018; Mirabello V et al., 2018).

"Bystander effect" or "by-stander effect" refers to the effect triggered by treatment of a target cell with a cytotoxic prodrug metabolite and refers to the secondary ablation effect on cells or tissues in the local microenvironment to the target cell.

Without wishing to be bound by theory, the bystander effect is believed to be caused by the diffusion of cytotoxic prodrug metabolites (activated prodrugs) from the site of production to affect unmodified cells separate from the target cell. Bystander effects (also defined as BEE, Bystander Effect Efficiency) can be quantified according to methods described in the literature and in the Examples (Wilson W et al, 2002; Hunter F et al., 2014). The bystander effect of a test prodrug is measured by the bystander effect efficiency that can be calculated using the algorithm ((Log $C_{10}T$−Log $C_{10}T_c$)/(Log $C_{10}T$−Log $C_{10}A_c$)). A BEE value of less than about 15%, less than about 10%, less than about 5%, less than about 1% is considered "substantially minimal", whilst a BEE value of greater than about 20%, 50%, 70%, or more is considered "substantial".

Moreover, the compound of Formula (I) (or Formula (II)) to be used in methods and compositions according to the present may be further defined with respect to criteria associated to biological activities determined in hypoxic conditions, compared or not to those observed in normoxic conditions (or independent from the presence of oxygen). For example such criteria may be the hypoxia cytotoxicity ratio (HCR) that can be measured in vitro using cancer cell lines (such as in human cancer cells selected from breast cancer cells, lung cancer cells, pancreatic cancer cells, gastrointestinal cancer cells, prostate cancer cells, ovarian cancer cells, brain cancer cells, head and neck cancer cells, and/or soft tissue sarcoma cells, as indicated above) and comprised in a range of values. The "hypoxia cytotoxicity ratio" or "HCR" is obtained by calculating the concentration at which a given compound kills 50% of cancer cells ($IC_{50}$) in normoxic conditions and anoxic conditions, and dividing such values, as described in the literature on the basis of resazurin or sulforhodamine B (SRB) assays, or another viability assay, such as an ATP-based viability assay. An exemplary assay for calculating such value is provided in Example 1. In particular, compounds of Formula (I) (or Formula (II)) may present a value for hypoxic cytotoxicity ($IC_{50}$) of 1 nM to 500 μM, or any intermediate range (such as 10 nM to 100 μM or 100 nM to 50 μM) and a hypoxia cytotoxicity ratio, comprised between 5 (or even 2) and 1000, or any intermediate range (such as 2 to 250, 5 to 250, 4 to 190, or 5 to 150). The Examples provide additional examples of intermediate ranges or other $IC_{50}$ value that that were measured in cancer cell lines having different origins or corresponding to distinct cancer sub-types.

The choice of the model (being in vitro, ex vivo or in animal model) can be made on the basis of literature describing the relationship between specific cancer cell lines (either human or animal, naturally or hTERT-immortalized) or primary cells cancer biopsies when tested in vitro or ex vivo. Many functional assays are available to evaluate the hypoxia-related effect on tumor that are consequent to the use of compound of Formula (I) (or Formula (II)), including cell proliferation, programmed cell death, apoptosis, necrosis, genes activation or inactivation and other cancer hallmark that can be analyzed by immunoblot, RT-PCR, immunocytochemistry, immunoprecipitation, RNA microarray, RNA-seq, flow cytometry, fluorescence microscopy, multiwell readers, and the like (Menyhárt O et al., 2016).

The compounds of Formula (I) (or Formula (II)) are used in compositions and methods according to the invention for treating breast cancer, pancreatic cancer, lung cancer, gastrointestinal cancer, prostate cancer, ovarian cancer, brain cancer, head and neck cancer, or soft tissue sarcoma. Specific examples of literature describing the relationship across genotype, phenotype, and clinical relevance of cancer lines following the exposure to a drug are available for pancreatic cancer (Deer E L et al., 2010), lung cancer (Cai Z et al., 2015), and breast cancer (Dai X et al., 2017). Moreover, ATCC (https://www.atcc.org) and DSMZ (https://www.dsmz.de) are organizations that procure such biological materials and provide with specific description of their use in functional assays and/or relevance for human cancer, for example in ATCC reports and Resource Books on ATCC cancer cell lines (including from breast, pancreatic, lung cancers, gastrointestinal cancers, prostate cancers, ovarian cancers, brain cancers, head and neck cancers, and soft tissue sarcomas) organized by specific gene mutations (such as APC, EGFR, BRAF, PTEN, RAS, RB1, or TP53), subtype, origin, and/or pathology (see for example ATCC cat. no. CB-0915-02, CB-1015-07, CB-0513-01, and others that are available from either ATCC or DFMZ, as indicated within Example 2).

Specific subtype or variants of such cancer can be defined by clinically or biologically relevant criteria (such as specific morphology, origin, stage, drug resistance, relapse, metastatic properties, and/or molecular markers) as indicated above, and may applicable across one or more cancer (sub) type and/or patient population. The subjects that are affected by any of such cancers may have been treated (or not) with standard-of-care protocols (such as radiotherapy, chemotherapy, and/or immunotherapy) prior to the treatment using the compounds of Formula (I) (or of Formula (II)) and related compositions and methods, so that drug resistance, immunological escape, relapse, or metastasis of the cancer in said subjects may be avoided, prevented, or delayed.

Given the experimental characterization of compounds of Formula (I) that is provided in the present invention, said compounds can be administered to a subject having hypoxic tumor cells, as established using appropriate technologies in vivo or ex vivo, for instance using specific markers, tracers, and/or cancer cells derived from lung, pancreatic, or breast cancer, (including by making use of biopsies and xenotransplatation of patient's cancer cells in animal models) Alternatively, the cancer (sub) type is further defined according to the resistance to standard-of-care, changes in the amount and/or molecular marker on cancer cells or immune cells (T cells, B cells, dendritic cells, macrophages, monocytes etc.). These cells may be detected as specific cell population (or sub populations) within tumor, in the tumor microenvironment, or in biological fluid (such as blood) using standard technologies (such as immunocytochemistry, flow cytometry, or immunohistochemistry) and may help evaluating the therapeutic effect of the administration of Formula (I) (or Formula (II)), also in view of the specific immunological profile of the cancer or other biomarkers.

Subtypes of lung cancers that may be treated in accordance to the present invention are small cell lung carcinoma (SCLC), non-small-cell lung carcinoma (NSCLC), or mesothelioma. Examples of NSCLC include squamous cell carcinoma, adenocarcinoma, and large cell carcinoma. In some instances, the mesothelioma is a cancerous tumor of the lining of the lung and chest cavity (pleura) or lining of the abdomen (peritoneum). The mesothelioma may be due to asbestos exposure.

Subtypes of pancreatic cancers that may be treated in accordance to the present invention include 1) exocrine pancreatic cancers, e.g., acinar cell carcinoma, adenocarcinoma, adenosquamous carcinoma, giant cell carcinoma of the pancreas, intraductal papillary-mucinous neoplasm (IPMN), mucinous cystadenocarcinoma, pancreatoblastoma, and serous cystadenocarcinoma, and 2) endocrine pancreatic cancers, e.g., gastrinoma (Zollinger-Ellison Syndrome), insulinoma, nonfunctional islet cell tumor, somatostatinoma, vasoactive intestinal peptide-releasing tumor (VIPoma or Verner-Morrison Syndrome), or pancreatic neuroendocrine tumors (PNETs). In preferred embodiments, the pancreatic cancer is an adenocarcinoma (i.e., pancreatic ductal carcinoma), invasive pancreatic ductal carcinoma, solid-pseudopapillary tumor (SPT), glucagonomas, or multiple endocrine neoplasia type-1 (MEN1) (Wermer's syndrome).

Subtypes of breast cancers that may be treated in accordance to the present invention are as triple negative breast neoplasm and cancers. As used herein, "breast cancer" means any malignant tumor of breast cells. Triple Negative Breast Cancer (TNBC) is a breast cancer characterized by cells that lack estrogen receptors and progesterone receptors, and do not have an excess of the HER2 protein on their surface. TNBC are often more invasive than other breast cancers. Because the tumor cells lack estrogen and progesterone receptors, hormone therapy (e.g., tamoxifen) by itself is not effective. Additionally, as the cells lack the HER2 protein, drugs that target HER2 are ineffective and thus require more effective, specific treatments.

Four main subtype of breast cancer may be defined by combining molecular markers and drug response as Luminal A (ER-positive, HER2-negative, low expression of proliferation marker Ki67, often responsive to hormone therapy or chemotherapy), Luminal B (ER-positive, HER2-positive, high expression of proliferation marker Ki67, variably responsive to hormone therapy, chemotherapy or anti-HER2 antibody therapies), Basal (ER-/PR-/HER2-triple negative, high expression of proliferation marker Ki67 and EGFR, not responsive to hormone therapy, but often responsive to chemotherapy), and HER2 amplified (ER-negative, HER2-positive, high expression of proliferation marker Ki67, variably responsive to hormone therapy, chemotherapy or anti-HER2 antibody therapies).

Alternatively, subtypes of breast cancers can be further defined according to histomorphologic abnormalities and include, but are not limited to, ductal carcinoma in situ (DCIS, most common non-invasive breast cancer), lobular carcinoma in situ (LCIS), invasive (or infiltrating) lobular carcinoma (ILC), invasive (or infiltrating) ductal carcinoma (IDC), microinvasive breast carcinoma (MIC), inflammatory breast cancer, adenoid cystic (adenocystic) carcinoma, low-grade adenosquamatous carcinoma, medullary carcinoma, mucinous (or colloid) carcinoma, papillary carcinoma, tubular carcinoma, metaplastic carcinoma, cribriform carcinoma of the breast, male breast cancer, normal-like breast cancer, Paget's disease of the nipple, phyllodes tumors of the breast, metastatic breast cancer, or micropapillary carcinoma. A single breast cancer tumor can be a combination of these types or be a mixture of invasive and in situ cancer. These subtypes of breast cancer may be treated by using one or approaches that is considered as standard-of-care for a given breast cancer subtype, including surgery, radiation therapy, chemotherapy (e.g. Paclitaxel), hormonal therapy (e.g. tamoxifen), immunotherapy or other antibody-based therapy targeting a cancer antigen (e.g., trastuzumab, targeting HER2 receptor), or chemotherapy combined (or not) with immunotherapy (e.g., tamoxifen and trastuzumab).

Alternatively, subtypes of hyperplasia and other benign lesions of breast tissues more or less predictive of a predisposition for breast cancer can be further defined from the location of such abnormal cell proliferation (without further histomorphologic abnormalities) including ductal hyperplasia, lobular hyperplasia, atypical ductal hyperplasia, and atypical lobular hyperplasia.

Additional types and subtypes of cancer may present hypoxic regions and may be treated by using a compound of Formula (I) (or of Formula (II)) as described herein. Subtypes of gastrointestinal cancer include, without being limited to, oesophageal cancer, stomach cancer, neuroendocrine tumors (NETs), small bowel cancer, gallbladder and biliary tract cancer, gastrointestinal stromal tumor (GIST), colorectal cancer, and anal cancer. Subtypes of prostate cancer include, without being limited to, acinar adenocarcinoma, ductal adenocarcinoma, transitional cell (or urothelial) cancer, squamous cell cancer, and small cell prostate cancer. Subtypes of ovarian cancer include, without being limited to, epithelial ovarian cancer, germ cell ovarian tumors, sex cord stromal tumors, or borderline ovarian tumors. Subtypes of brain cancer include, without being limited to, acoustic neuroma, astrocytoma, chordoma, CNS lymphoma, craniopharyngioma, brain stem glioma, ependymoma, mixed glioma, optic nerve glioma, subependymoma, medulloblastoma, meningioma, metastatic brain tumors, oligodendroglioma, pituitary tumors, primitive neuroectodermal tumor, schwannoma, juvenile pilocytic astrocytoma (JPA), pineal tumor, or rhabdoid tumor. Subtypes of head and neck cancer, include, without being limited to, laryngeal cancer, lip and oral cavity cancer, metastatic squamous neck cancer with occult primary, nasopharyngeal cancer, oropharyngeal cancer, paranasal sinus and nasal cavity cancer, or salivary gland cancer. Subtypes of soft tissue sarcoma, include, without being limited to, angiosarcoma, dermatofibrosarcoma, epithelioid sarcoma, Ewing's sarcoma, fibrosarcoma, gastrointestinal stromal tumors, Kaposi sarcoma, leiomyosarcoma, liposarcomas, malignant fibrous histiocytoma, neurofibrosarcoma, rhabdomyosarcoma, and synovial sarcoma.

The pharmaceutical compositions and methods that involve the use of a compound of Formula (I) (or of Formula (II)) or related pharmaceutically acceptable salt can be established by formulating such compound (with or without a pharmaceutically acceptable excipient, adjuvant, carrier, buffer, diluent, or stabilizer) suitable for the administration in subjects, in particular for treating lung cancer, pancreatic, breast cancer, gastrointestinal cancer, prostate cancer, ovarian cancer, brain cancer, head and neck cancer, or soft tissue sarcoma. Preferably such compositions are intended for parenteral administration (and more preferably for subcutaneous or intravenous administration), intratumoral administration, trans-arterial embolization administration, or oral administration. The choice of the administration route can be determined by various factors such as the specific cancer (sub-) types, its hypoxic state, location, or concurrent treatments.

Pharmaceutical compositions of the present invention may be formulated in a conventional manner using one or more pharmaceutically acceptable inactive ingredients that facilitate processing of the active compounds into preparations that are used pharmaceutically. Proper formulation is dependent upon the route of administration chosen. A summary of pharmaceutical compositions and formulations described herein is found, for example, in books such as Remington: The Science and Practice of Pharmacy ($21^{st}$ Edition, 2005; Lippincott Williams & Wilkins), Encyclopedia of Pharmaceutical Science and Technology ($4^{th}$ Edition, 2013; CRC Press, Taylor & Francis Group), and Ansel's Pharmaceutical Dosage Forms and Drug Delivery Systems ($11^{th}$ Edition, 2017; Wolters Kluwer), herein incorporated by reference for such disclosure.

As used herein, "administer" or "administration" means to provide a treatment, for example to prescribe a treatment, apply a treatment, or distribute a treatment. In some instances, to administer means a medical professional prescribes a treatment which a patient applies (e.g., the patient applies a device, consumes a medication, or injects a medication). Administration of a medical treatment does not require immediate or constant supervision of a medical professional.

Any composition described herein optionally comprises minor amounts of non-toxic auxiliary substances such as wetting or emulsifying agents, pH buffering agents, stabilizers, solubility enhancers, diluents, and other such agents, such as for example, sodium acetate, sorbitan monolaurate, triethanolamine oleate and cyclodextrins. The composition may further comprise one or more of lactose, dextrose, mannitol, pH buffering agents, antioxidant agents, preservative agents, tonicity adjusters, or combinations thereof. Examples of pharmaceutically acceptable carriers that are optionally used include, but are not limited to aqueous vehicles, nonaqueous vehicles, antimicrobial agents, local anesthetics, suspending and dispersing agents, emulsifying agents, sequestering or chelating agents and other pharmaceutically acceptable substances.

In some embodiments, the compounds described herein are administered either alone or in combination with pharmaceutically acceptable carriers, excipients or diluents, in a pharmaceutical composition. Administration of the compounds and compositions described herein can be effected by any method that enables delivery of the compounds to the site of action. These methods include, though are not limited to delivery via enteral routes (including oral, gastric or duodenal feeding tube, rectal suppository and rectal enema), parenteral routes (injection or infusion, including intraarterial, intracardiac, intradermal, intraduodenal, intramedullary, intramuscular, intraosseous, intraperitoneal, intrathecal, intravascular, intravenous, intravitreal, epidural and subcutaneous), inhalational, transdermal, transmucosal, sublingual, buccal and topical (including epicutaneous, dermal, enema, eye drops, ear drops, intranasal, vaginal) administration, although the most suitable route may depend upon for example the condition and disorder of the recipient. By way of example only, compounds described herein can be administered locally to the area in need of treatment, by for example, local infusion during surgery, topical application such as creams or ointments, injection, catheter, or implant. The administration can also be by direct injection at the site of a diseased tissue or organ, or by direct injection at the tumor cells (with or without prior identifying the hypoxic regions in the tumor). Systemic administration may be performed by oral, intravenous, intraperitoneal and intramuscular administration.

In some embodiments, pharmaceutical compositions suitable for oral administration are presented as discrete units such as capsules, cachets or tablets each containing a predetermined amount of the present compounds; as a powder or granules; as a solution or a suspension in an aqueous liquid or a non-aqueous liquid; or as an oil-in-water liquid emulsion or a water-in-oil liquid emulsion. The present compounds of Formula (I) or Formula (II), and in particular Cpd.11d (preliminarily characterized as having relatively high oral bioavailability) may be presented as a bolus, electuary or paste. For buccal or sublingual administration, the compositions may take the form of tablets, lozenges, pastilles, gels, push-fit capsules made of gelatin, as well as soft, sealed capsules made of gelatin and a plasticizer, such as glycerol or sorbitol formulated in conventional manner. Such compositions may comprise present compound in a flavored basis such as sucrose and acacia or tragacanth.

Pharmaceutical compositions in the form of tablets may be made by compression or molding, optionally with one or more accessory ingredients. Compressed tablets may be prepared by compressing in a suitable machine the present compounds in a free-flowing form such as a powder or granules, optionally mixed with binders, inert diluents, or lubricating, surface active or dispersing agents. Molded tablets may be made by molding in a suitable machine a mixture of powdered compound moistened with an inert liquid diluent. Tablets (or dragees) are coated or formulated so as to provide slow or controlled release of the present compounds. Suitable coatings (such as sugar solutions may be used, which may optionally contain gum arabic, talc, or polyvinyl pyrrolidone) and dyestuffs or pigments may be added to the tablets or dragee coatings. Tablets may contain the present compounds in admixture with non-toxic pharmaceutically acceptable excipients, for example, inert diluents, such as calcium carbonate, sodium carbonate, lactose, calcium phosphate or sodium phosphate; granulating and disintegrating agents, such as microcrystalline cellulose, sodium croscarmellose, corn starch, or alginic acid; other agents, for example starch, gelatin, polyvinyl-pyrrolidone, lactose, lubricants such as talc or magnesium stearate, acacia, magnesium stearate or talc. Tablets may be un-coated or coated by known techniques to mask the taste or delay disintegration and absorption in gastrointestinal tract and provide a sustained action over a longer period. A taste masking material may be hydroxypropylmethyl- or hydroxypropyl-cellulose, or a time delay material such as ethyl cellulose. Formulations for oral use may also be presented as hard gelatin capsules wherein present compounds are mixed with an inert solid diluent, for example, calcium carbonate, calcium phosphate or kaolin, or as soft gelatin capsules wherein present compounds are mixed with a carrier such as polyethyleneglycol or an oil medium, for example peanut oil, liquid paraffin, or olive oil.

The pharmaceutical compositions of the present invention may be also formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulation agents such as suspending, stabilizing and/or dispersing agents. Suitable organic solvents (such as ethanol, DMSO, or dimethylacetamide) or solvent mixtures may be used for producing long-term storage, high concentration, and/or batch pharmaceutical compositions comprising the present compounds that may be diluted to the desired concentration or daily dose of the active ingredient by making use of appropriate aqueous buffers (comprising glucose, sodium chloride, Ringer's solution, phosphate buffered saline solution, or other excipients diluted in sterile injectable aqueous solution) just before parenteral administration (by means of pre-filled syringes, vials, or other components in a kit). Compositions may be presented in unit-dose or multi-dose containers, for example sealed ampoules and vials, and may be stored in powder form or in a freeze-dried (lyophilized) condition requiring only the addition of sterile liquid carrier, such as saline or sterile pyrogen-free water, immediately prior to use. Extemporaneous injection solutions and suspensions may be prepared from sterile powders, granules and tablets as previously described. A preferred drug preparation is a powder filled vial that is sterilized under gamma-irradiation. A compound of Formula (I) (or of Formula (II)) can be provided in the form of powder that is sufficiently stable and water-soluble to be used for preparing, immediately before administration (e.g. by injection), a dilution in water for injection at an appropriate dilution (10 mg/mL, 100 mg/mL, or further concentrated) for further addition to a dextrose infusion bag. Sodium acetate can be added to ensure that the pH is acceptable for the chosen route of administration (e.g. for intravenous administration or for other type of injection).

Pharmaceutical compositions for parenteral administration include aqueous and non-aqueous (oily) sterile injection solutions of the active compounds which may contain anti-oxidants, buffers, bacteriostatic compounds and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase solubility of the compounds to allow for preparation of highly concentrated solutions.

In some embodiments, the present compounds described herein are delivered in a vesicle, such as a liposome. In further or alternative embodiments, the compounds and pharmaceutical compositions described herein are delivered in a controlled release system, or a controlled release system can be placed in proximity of the therapeutic target.

Pharmaceutical compositions may also be formulated as a depot preparation. Such long acting formulations may be administered by implantation (for example subcutaneously or intramuscularly) or by intramuscular injection. Thus, for example, present compounds may be formulated with suitable polymeric or hydrophobic materials (for example, as an emulsion in an acceptable oil) or ion exchange resins, or as sparingly soluble salt.

Aqueous suspensions contain the active ingredients in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

In some embodiments, pharmaceutical compositions described herein are in the form of a sterile injectable aqueous solution. Acceptable vehicles and solvents that are employed include but are not limited to water, Ringer's solution, phosphate buffered saline solution, U.S.P. and isotonic sodium chloride solution, ethanol, and 1,3-butanediol. In addition, sterile, fixed oils (such as any bland fixed oil, including synthetic mono- or diglycerides) may be employed as a solvent or suspending medium. Suitable lipophilic solvents or vehicles include fatty oils such as sesame oil, or synthetic fatty acid esters, such as ethyl oleate or triglycerides, or liposomes or other microparticulate systems may be used to target the agent to blood components or one or more organs. A sterile injectable preparation may be a sterile injectable oil-in-water microemulsion where present compound is dissolved in the oily phase. Present compound may be first dissolved in a mixture of soybean oil and lecithin. The oil solution then introduced into a water/glycerol mixture and processed to form a microemulsion. In additional embodiments, the injectable solutions or microemulsions are introduced into subject's blood stream by local bolus injection.

In other embodiments, the pharmaceutical composition is in the form of a sterile injectable aqueous or oleagenous suspension for intramuscular and subcutaneous administration. In further or additional embodiments, this suspension is formulated using those suitable dispersing or wetting agents and suspending agents which have been mentioned above. The sterile injectable preparation may be a sterile injectable solution or suspension in a non-toxic parenterally-acceptable diluent or solvent, for example as a solution in 1,3-butanediol. In addition, sterile, fixed oils are conventionally employed as a solvent or suspending medium. For this purpose in some embodiments, any bland fixed oil is optionally employed including synthetic mono- or diglycerides. In addition, fatty acids such as oleic acid find use in the preparation of injectables.

Suitable pharmaceutical carriers include inert diluents or fillers, water and various organic solvents. In some embodiments, the pharmaceutical composition contains additional ingredients such as flavorings, binders, excipients and the like. Thus for oral administration, tablets containing various excipients, such as citric acid are employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. In other embodiments, solid compositions of a similar type are employed in soft and hard filled gelatin capsules. Preferred materials, therefore, include lactose or milk sugar and high molecular weight polyethylene glycols. In certain embodiments where aqueous suspensions or elixirs are desired for oral administration, the active compound therein is combined with various sweetening or flavoring agents, coloring matters or dyes and, if desired, emulsifying agents or suspending agents, together with diluents such as water, ethanol, propylene glycol, glycerin, or combinations thereof.

In some embodiments, oily suspensions are formulated by suspending the active ingredient in a vegetable oil, for example arachis oil, olive oil, sesame oil or coconut oil, or in mineral oil such as liquid paraffin. In certain embodiments, the oily suspensions contain a thickening agent, for example beeswax, hard paraffin or cetyl alcohol. In further embodiments, sweetening agents such as those set forth above, and flavoring agents are added to provide a palatable oral preparation. In other embodiments, these compositions are preserved by the addition of an anti-oxidant such as butylated hydroxyanisole or alpha-tocopherol. In some embodiments, pharmaceutical compositions are in the form of oil-in-water emulsions. In some embodiments, the oily phase is a vegetable oil, for example olive oil or arachis oil, or a mineral oil, for example liquid paraffin or mixtures thereof.

Pharmaceutical compositions may be administered topically, that is by non-systemic administration. This includes the application of a compound of the present invention externally to the epidermis or the buccal cavity and the instillation of such a compound into the ear, eye and nose, such that the compound does not significantly enter the blood stream. Pharmaceutical compositions suitable for topical administration include liquid or semi-liquid preparations suitable for penetration through the skin such as gels, liniments, lotions, creams, ointments or pastes, and drops suitable for administration to the eye, ear or nose. The pharmaceutical composition may comprise, for topical administration, from 0.001% to 10% w/w, for instance from 1% to 2% by weight of formulation. For topical use, creams, ointments, jellies, solutions or suspensions, mouth washes and gargles etc., containing present compound is used.

Pharmaceutical compositions for administration by inhalation are conveniently delivered from an insufflator, nebulizer pressurized packs or other convenient means of delivering an aerosol spray. Pressurized packs may comprise a suitable propellant such as dichloro- or, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, pharmaceutical preparations may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Dispersible powders and granules suitable for preparation of an aqueous suspension by the addition of water provide the active ingredient in admixture with a dispersing or wetting agent, suspending agent and one or more preservatives. Suitable sweetening agents, flavoring agents, preservatives, antioxidant, dispersing or wetting agents and suspending agents are exemplified by those already mentioned above. Additional excipients, for example sweetening, flavoring and coloring agents, may be present. In further or additional embodiments, these compositions are preserved by the addition of an anti-oxidant such as ascorbic acid. Suitable emulsifying agents include but are not limited to naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate.

In some embodiments, the pharmaceutical composition described herein further comprises a cyclodextrin, with a concentration (w/v) ranging from about 0.001% to about 50%. Some embodiments described herein provide a composition further comprising cyclodextrin, wherein the cyclodextrin has a concentration (w/v) of about 15%, 20%, 22%, 25%, 26%, 27%, 28%, 29%, 30%, 31%, 32%, 33%, 34%, 35%, 36%, 37%, or 38% when cyclodextrin derivative is SBE7-β-CD (Captisol®). In one embodiment, the cyclodextrin has a concentration (w/v) of about 30% when cyclodextrin derivative is SBE7-β-CD (Captisol®). In another embodiment, the solubility enhancer has a concentration (w/v) of about 29.4% when the cyclodextrin derivative is SBE7-β-CD (Captisol®). Additional cyclodextrin derivatives suitable for use in intravenous compositions described herein are known in the art and are described in, e.g., U.S. Pat. Nos. 5,134,127, 5,376,645, "Modified Cyclodextrins: Scaffolds and Templates for Supramolecular Chemistry" (Eds. C. J. Easton, S. F. Lincoln, Imperial College Press), each of which is incorporated by reference herein for such disclosure. Examples of suitable cyclodextrin derivative, for use in certain embodiments of the compositions, methods and kits described herein include, but are not limited to, α-cyclodextrins, β-cyclodextrins, γ-cyclodextrins and their derivatives, SAE-CD derivatives.

In some embodiments, the pharmaceutical compositions described herein are in unit dosage forms suitable for single administration of precise dosages. In unit dosage form, the formulation is divided into unit doses containing appropriate quantities of one or more active ingredients. In some embodiments, the unit dosage is in the form of a package containing discrete quantities of the formulation. Non-limiting examples are packaged tablets or capsules, and powders in vials or ampoules. In some embodiments, aqueous suspension compositions are packaged in single-dose non-reclosable containers. Alternatively, multiple-dose reclosable containers are used, in which case it is typical to include a preservative in the composition. By way of example only, formulations for parenteral injection are presented in unit dosage form, which include, but are not limited to ampoules, or in multi dose containers, with an added preservative.

In some embodiments, the pharmaceutical compositions described that are in unit dosage forms may be provided in the form of a kit or other a packaging containing discrete quantities of the pharmaceutical compositions in liquid or solid form. The kit may comprise containers for single or multiple usages, for ready-to-use or concentrated pharmaceutical compositions (and/or related buffers or diluents), devices for administration (such as syringes, needles, tubes or filters), and instructions. The kit may be adapted to long-term storage, in particular at low temperature.

Present compounds are administered for prophylactic and/or therapeutic treatments of cancer, in particular breast cancer, lung cancer, pancreatic cancer, gastrointestinal cancer, prostate cancer, ovarian cancer, brain cancer, head and neck cancer, or soft tissue sarcoma. In certain therapeutic applications, present compounds are administered to a subject already suffering from such cancer, in an amount sufficient to cure or at least partially arrest at least one of the symptoms of cancer. Amounts effective for this use depend on the severity and course of cancer, previous therapy, the subject's health status, sex, weight, diet, and response to the drugs, and the judgment of the treating physician. Therapeutically effective amounts are optionally determined by methods including, but not limited to, a dose escalation and/or dose ranging clinical trial. The amount of a given agent that corresponds to such an amount varies depending upon factors such as the particular compound (including its bioavailability and rate of metabolization or excretion), cancer stage and hypoxic features, or the suitable formulation and route of administration.

The terms "effective amount" or "therapeutically effective amount," as used herein, refer to a sufficient amount of a compound being administered which will relieve to some extent one or more of the symptoms of the disease or condition being treated. The result can be reduction and/or alleviation of the signs, symptoms, or causes of a cancer, or any other desired alteration of a biological system. For example, an "effective amount" for therapeutic uses is the amount of the composition comprising present compound that is required to provide a clinically significant decrease in disease symptoms.

The term "subject" or "patient" encompasses mammals and non-mammals. "Mammals" include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one embodiment, the mammal is a human.

In prophylactic applications, compositions containing present compounds described herein are administered to a patient susceptible to or otherwise at risk of a particular cancer. Such an amount is defined to be a "prophylactically effective amount or dose." In this use, the precise amounts also depend on the patient's state of health, weight, and the like. In one aspect, prophylactic treatments include administering to a mammal, who previously experienced at least one symptom of the disease being treated and is currently in remission, a pharmaceutical composition comprising a compound described herein, or a pharmaceutically acceptable salt thereof, in order to prevent a return of the cancer.

Such compositions can be administered to a subject to be treated for a cancer (in particular, for lung, pancreatic, or breast cancer) in a therapeutically effective amount. The daily dosages appropriate for the active agents are from about 0.1 mg to about 3000 mg, or from about 100 to 6000 mg, conveniently administered in divided doses, including, but not limited to, up to four times a day or in extended release form. Suitable unit dosage forms for oral administration include from about 1 to 6000 mg active ingredient, from about 100 to 3000 mg, from about 500 to 3000 mg, from about 1 to 2500 mg, from about 0.1 to 500 mg, from about 1 to 250 mg, from about 1 to about 100 mg, from about 1 to about 50 mg, from about 1 to about 30 mg, from about 1 to about 20 mg of the present compounds. Such dosages are optionally altered depending on a number of variables, not limited to the activity of the compound used, the mode of administration, the requirements of a subject, the severity of the cancer being treated, and the judgment of the practitioner. In one embodiment, the desired dose is conveniently presented in a single dose or in divided doses administered simultaneously or at appropriate intervals, for example as two, three, four or more sub-doses per day every 1 hour, 2 hours, 3, hours, 4 hours, 6 hours, 9 hours, and the like, and also in view of specific cancer (sub-) type, for treatment, or for maintenance or prophylactic use.

In one embodiment, the dosages appropriate for the compound described herein, or a pharmaceutically acceptable salt thereof, are administered preferably at a dose comprised between 40 and 10,000 $mg/m^2$, between 40 and 4000 $mg/m^2$, or between 1200 and 2400 $mg/m^2$ (or alternatively defined as 1 to 100 mg/Kg per body weight, or more up to 100 mg/Kg) and intermediate ranges or values (for example, from about 0.01 to about 50 mg/kg about 5 mg/kg to about 30 mg/kg, e.g., about 25 mg/kg, about 20 mg/kg, about 15 mg/kg, or about 10 mg/kg, or 4 mg/kg, 3 mg/kg, 2 mg/kg, or 1 mg/kg). In some embodiments, the dosage or the amount of active compound in the dosage form is lower or higher than the ranges indicated herein, based on a number of variables in regard to an individual treatment regime. In various embodiments, the unit dosages are adapted depending on a number of variables including, but not limited to, the activity of the compound used, the disease or condition to be treated, the mode of administration, the requirements of the individual subject, the severity of the cancer being treated, and the judgment of the practitioner.

The pharmaceutical composition can administered with a regular regimen with multiple administrations (cycles) that are defined per 1, 2, 3, or 4 weeks, or per month, for example, one day per week (or at a frequency of every day for 2, 3, 4, or 5 consecutive, or non-consecutive, days per week) or one day per month (or at a frequency of every day for 2, 3, 4, or 5 consecutive, or non-consecutive, days per month), preferably with intravenous infusion that is administered over 2 hours per day for 3 consecutive days. This regimen can be pursued for one or more consecutive weeks or months, for instance up to 2, 4, 8, 12, 26 or 52 weeks, or up to 2, 4, 6, 8, 10, or 12 months, at the same dose or with higher or lower dosage as it may be required according to the subject and/or the cancer stage.

In certain embodiments wherein a patient's status does improve, the dose of drug being administered is temporarily reduced or temporarily suspended for a certain length of time (i.e., a "drug holiday"). In specific embodiments, the length of the drug holiday is between 1 day and 1 year, including by way of example only, 1 day, 2 days, 3 days, 4 days, 5 days, 6 days, 7 days, 8 days, 9 days, 10 days, 11 days, 12 days, 13 days, 14 days, 15 days, 16 days, 17 days, 19 days, 20 days, 21 days, 28 days, 50 days, 70 days, 100 days, 120 days, 150 days, 180 days, 200 days, 250 days, 300 days, 320 days, 350 days, or 365 days. The dose reduction during a drug holiday is, by way of example only, by 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

Once improvement of the patient's conditions has occurred, a maintenance dose is administered if necessary. Subsequently, in specific embodiments, the dosage or the frequency of administration, or both, is reduced, as a function of the symptoms, to a level at which the improved disease, disorder or condition is retained. In certain embodiments, however, the patient requires intermittent treatment on a long-term basis upon any recurrence of symptoms. In certain embodiments wherein the patient's condition does not improve, upon the doctor's discretion the administration of the compounds are administered chronically, that is, for an extended period of time, including throughout the duration of the patient's life in order to ameliorate or otherwise control or limit the symptoms of the cancer.

In any of the aforementioned aspects are further embodiments, the effective amount of the present compounds, or a pharmaceutically acceptable salt thereof, is: (a) systemically administered to the subject; and/or (b) administered orally to the subject; and/or (c) intravenously administered to the subject; and/or (d) administered by injection to subject; and/or (e) administered topically to the subject and/or (f) administered non-systemically or locally to the subject. In any further embodiments comprising multiple administrations of the effective amount of present compounds in a method for treating breast cancer, lung cancer, pancreatic cancer, gastrointestinal cancer, prostate cancer, ovarian cancer, brain cancer, head and neck cancer, or soft tissue sarcoma, the compound is administered continuously or intermittently to the subject as single agent or in a combination therapy, wherein either present compound or the other therapeutic agent is administered with similar or distinct frequency. In further embodiments, the method comprises a drug holiday, wherein the administration of present compound is temporarily suspended or the dose being administered is temporarily reduced; at the end of the drug holiday, dosing of the compound is resumed, for example after 1, day, 1 week, 1 month, or more consecutive months, up to 1 year.

The compound of Formula (I) (or Formula (II)) and the pharmaceutical composition for the use for treating breast cancer, lung cancer, pancreatic cancer, gastrointestinal cancer, prostate cancer, ovarian cancer, brain cancer, head and neck cancer, or soft tissue sarcoma, may be administered to a subject, simultaneously or sequentially, with another therapeutic agent or therapy, in particular with a therapeutic agent or therapy that is useful for treating breast cancer, lung cancer, and/or pancreatic cancer, as determined in clinical practice or (pre-) clinical development. In some embodiments, the other therapeutic agent or therapy exert its activity independently from hypoxia. Given that cytotoxic activity of compound of Formula (I) (or Formula (II)) targeting hypoxic regions in tumor may improve the therapeutic activity, decrease dosages, and/or reduce the period of treatment of another drug acting through different mechanisms, the compound of Formula (I) (or Formula (II)) would be preferably administered before such other drug, therapeutic agent or therapy, and in particular before starting a standard-of-care protocol (such as radiotherapy, chemotherapy, or immunotherapy).

Any of the medical uses and methods of treatment described herein, may further comprise administering additional cancer therapy to the individual or patient. In certain embodiments, the cancer therapy is, by way of non-limiting example, at least one anti-cancer agent (e.g., chemotherapeutic agent), radiation therapy, or surgery, in particular standard-of-care treatment for lung cancer, pancreatic cancer, breast cancer, gastrointestinal cancer, prostate cancer, ovarian cancer, brain cancer, head and neck cancer, and/or soft tissue sarcoma. In some embodiments, a combination of (1) administration of an effective amount of present compounds and (2) 1 to 3 therapies selected from the group consisting of (i) administration of an effective amount of additional anticancer agents, (ii) administration of an effective amount of hormonal therapeutic agents, and (iii) non-drug therapy preventing and/or treating cancer more effectively, including surgery and/or radiotherapy.

"Co-administration", "Combination therapy" or "combination treatment" refers to the use of two or more agents or therapies, i.e., use of a hypoxia activated prodrug as described herein together with one or more compounds to treat cancer in any manner in which the pharmacological effects of both are visible or otherwise measurable in the subject. The administration in combination does not require that a single pharmaceutical composition, the same dosage form, the same route of administration be used for administration of both agents, or that the two agents are administered at precisely the same time, in the same order, and/or at the same frequency. In some embodiments, present compounds are administered only after the administration of the agent or therapy. In some embodiments, present compounds are administered only before the administration of the agent or therapy. In some embodiments, present compounds and the other agent or therapy are administered in cycles, sequentially or alternatively, wherein the frequency of administration is identical for the two agents or either agent is more frequently administered than the other. In some embodiments, present compounds are administered as second line therapy only, or as first line therapy only. In some embodiments, the effect of the other agent or therapy on the hypoxic regions within tumors is evaluated, before the administration of present compounds. In some embodiments, the effect of present compounds on the hypoxic regions within tumors is evaluated, before the administration of other therapy or agent.

In various embodiments, the treatment is referred as first, second, or third line treatment or therapy. In another embodiment, the treatment is a first, a second, or a third line treatment. As used herein, the phrase "first line therapy" or "second line therapy" refers to the order of treatment received by a subject. For example, primary treatment can be surgery, chemotherapy, radiation therapy, or a combination of these therapies. Typically, a subject is given a subsequent regimen because the subject did not show a positive clinical or only showed a sub-clinical response to the first line therapy. In some embodiments, the compound of Formula (I) (or Formula (II) and related the pharmaceutical composition are used as a first line therapy or a second line therapy.

A preferred agent or therapy for combination therapy comprising the administration is chemotherapy. Among the chemotherapeutic agents that may be administered, non-limiting examples are cisplatin, carboplatin, paclitaxel, gemcitabine, docetaxel, or doxorubicin. Further, non-limiting examples of chemotherapeutic agents include alkylating agents, antimetabolites, anticancer antibiotics, plant-derived anticancer agents, and the like.

Alkylating agents include but are not limited to chlorambucil, cyclophosphamide, ifosfamide, thiotepa, carboquone, nimustine hydrochloride, mitobronitol, melphalan, dacarbazine, ranimustine, sodium estramustine phosphate, streptozocin, pipobroman, etoglucid, carboplatin, cisplatin, miboplatin, nedaplatin, oxaliplatin, altretamine, pumitepa, ribomustin, temozolomide, treosulphan, trophosphamide, zinostatin stimalamer, adozelesin, cystemustine, and the like.

Antimetabolites include but are not limited to mercaptopurine, 6-mercaptopurine riboside, thioinosine, methotrexate, enocitabine, cytarabine, cytarabine ocfosfate, ancitabine hydrochloride, 5-FU drugs (e.g., fluorouracil, tegafur, UFT, doxifluridine, carmofur, gallocitabine, emitefur, and the like), aminopterine, leucovorin calcium, cladribine, emitefur, fludarabine, gemcitabine, hydroxycarbamide, pentostatin, piritrexim, idoxuridine, mitoguazone, thiazophrine, and the like.

Anticancer antibiotics include but are not limited to actinomycin-D, actinomycin-C, mitomycin-C, chromomycin-A3, bleomycin hydrochloride, bleomycin sulfate, peplomycin sulfate, daunorubicin hydrochloride, doxorubicin hydrochloride, aclarubicin hydrochloride, pirarubicin hydrochloride, epirubicin hydrochloride, neocarzinostatin, mithramycin, sarcomycin, carzinophilin, mitotane, zorubicin hydrochloride, mitoxantrone hydrochloride, and the like.

Plant-derived or other natural anticancer agents include but are not limited to etoposide, vinblastine sulfate, vincristine sulfate, vindesine sulfate, teniposide, paclitaxel, vinorelbine, trabectedin, lurbinectedin, and the like.

A preferred agent or therapy for combination therapy comprising the administration is immunotherapy, which include a large variety of agents and therapies that target cells, tissue, and/or protein that may modulate immune response, preferably with respect to cancer and more preferably with respect to lung cancer, pancreatic cancer, breast cancer, gastrointestinal cancer, prostate cancer, ovarian cancer, brain cancer, head and neck cancer, and/or soft tissue sarcoma, given the characterization of the present compounds. The nature and structure of immunotherapeutic agents can be different, including cells, proteins, peptides, small molecules, or nucleic acids.

Immunotherapeutic agents include but are not limited to, interferons, interleukins, macrophage colony-stimulating factor, granulocyte colony-stimulating factor, erythropoietin, lymphotoxin, or other proteins (including antibodies) inhibiting or otherwise targeting the action of cell growth factors or cell growth factor receptors. Immunotherapeutic, targeted agents that inhibit the action of cell growth factor include but are not limited to HER2 antibody (e.g., trastuzumab), imatinib mesylate, ZD1839 or EGFR antibody (e.g., cetuximab), antibody to VEGF (e.g., bevacizumab), VEGFR antibody, VEGFR inhibitor, and EGFR inhibitor (e.g., erlotinib).

In particular, the medical uses and methods of treatment of the invention also contemplate that the compounds of formula (I) may be used in combination with other anticancer agents such as antibody therapeutics or anticancer antibodies. In a further embodiment, the additional medication is a targeted anti-cancer antibody, i.e., an antibody which targets a specific tumor type. The term "antibody" is used in the broadest sense and specifically covers intact monoclonal antibodies, polyclonal antibodies, chimeric antibodies, humanized antibodies, multispecific antibodies (e.g. bispecific antibodies) formed from at least two intact antibodies, and antibody fragments so long as they exhibit the desired biological activity. The term "Antibody fragments" comprises a portion of an intact antibody, preferably the antigen binding or variable region of the intact antibody. Examples of antibody fragments include Fab, Fab', F (ab') 2, and Fv fragments; diabodies; linear antibodies. The technologies and products that allow producing antibodies, either monospecific or bispecific, are known in the art, as extensively reviewed in the literature, also with respect to alternative formats, antibody-drug conjugates, antibody design methods, in vitro screening methods, constant regions, post-translational and chemical modifications, improved feature for triggering cancer cell death such as Fc engineering, tumour-associated antigens and the corresponding therapeutically useful antitumor antibody agents (Tiller K and Tessier P, 2015; Weiner G, 2015; Fan G et al., 2015; Sliwkowski & Mellman, 2013).

In one aspect, the targeted anti-cancer antibody is one or more of gemtuzumab (Mylotarg), alemtuzmab (CAMPATH™), rituximab (Rituxin, Mabthera), trastuzumab (Herceptin™), nimotuxumab, cetuximab (Erbitux), erlotinib (TARCEVA™, Genentech/OSI Pharm.), bevacizumab (Avastin™), pertuzumab (OMNITARG™, rhuMab 2C4, Genentech), Brentuximab vedotin (Adcetris™), Ipilimumab (MDX-101 and also known as Yervoy), Ofatumumab (Arzerra), Panitumumab (Vectibix), and Tositumomab (Bexxar), among others. In another aspect, the targeted antibody is one or more of alemtuzumab, apolizumab, aselizumab, atlizumab, bapineuzumab, bevacizumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pertuzumab, pexelizumab, ralivizumab, ranibizumab, reslivizumab, reslizumab, toralizumab, trastuzumab, tucotuzumab celmoleukin, tucusituzumab, umavizumab, urtoxazumab, and visilizumab. In another embodiment, the at least one additional medication includes antibodies to immune co-stimulatory molecules including but not limited to CTLA-4, 4-1BB and PD-1, antibodies to cytokines (including but not limited to IL-10, TGF-beta, etc.), and chemokine receptors including but not limited to CCR2, CCR4 etc., among others.

In some embodiments, the immunotherapeutic agent is a co-stimulatory or co-inhibitory molecule. In some embodiments, the immune-modulating agent is an immune checkpoint inhibitor (CPI) and/or an immune checkpoint activator (CPA). In some embodiments, the immune-modulating agent is an agent targeting one or more of a T-cell co-stimulatory or co-inhibitory molecule, a member of the B7 family, a member of the TNF receptor or TNF ligand superfamily, a member of the TIM family, and a member of the Galectin family. In various embodiments, immune-modulating agent is an agent targeting one or more of PD-1, PD-L1, PD-L2, CD137 (4-1BB), CD137 ligand (4-1BB ligand), CTLA-4, OX-40, OX-40 ligand, HVEM, GITR, GITR ligand, CD27, CD28, CD30, CD30 ligand, CD40, CD40 ligand, LIGHT (CD258), CD70, B7-1, B7-2, ICOS, ICOS ligand, TIM-1, TIM-3, TIM-4, BTLA, galectin-1, galectin-9, CEACAM-1, CEACAM-4, CEACAM-5, LAG-3, B7-H1, B7-H2, B7-H3, B7-H4, B7-H5, B7-H6, HHLA2, HMGB1, BTLA, CRTAM, CD200, CCR4, and CXCR4.

In some embodiments, the immunotherapeutic agent that blocks, reduces and/or inhibits PD-1 and PD-L1 or PD-L2 and/or the binding of PD-1 with PD-L1 or PD-L2 (as well those binding to CTLA-4) by binding to the extracellular domain of either of these cell surface protein. By way of non-limiting example, these antibodies include one or more of nivolumab (ONO-4538/BMS-936558, MDX1106, OPDIVO, BRISTOL MYERS SQUIBB), pembrolizumab (KEYTRUDA, Merck), MK-3475 (MERCK), BMS-36559 (BRISTOL MYERS SQUIBB), MPDL3280A (ROCHE), YW243.55.S70, MPDL3280A, MEDI-4736, MSB-0010718C, MDX-1105, MDX-1105, MSB0010718C, AMP-224, Tremelimumab (Ticilimumab, CP-675,206); and Ipilimumab (MDX-010, Yervoy). Other anti-cancer antibodies are Daratumuab (anti-CD38) and urelumab (BMS-663513, an anti-4CD137 antibody), and Ofatumumab (anti-CD20).

In addition to the aforementioned drugs, other anti-cancer agents include but are not limited to L-asparaginase, aceglatone, procarbazine hydrochloride, protoporphyrin-cobalt complex salt, mercuric hematoporphyrin-sodium, topoisomerase I inhibitors (e.g., irinotecan, topotecan, and the like), topoisomerase II inhibitors (e.g., sobuzoxane, and the like), differentiation inducers (e.g., retinoid, vitamin D, and the like), α-blockers (e.g., tamsulosin hydrochloride, naftopidil, urapidil, alfuzosin, terazosin, prazosin, silodosin, and the like) serine/threonine kinase inhibitor (e.g adavosertib, afatinib, aflibercept, axitinib, bevacizumab, bosutinib, cabozantinib, cetuximab, cobimetinib, crizotinib, dasatinib, entrectinib, erdafitinib, erlotinib, fostamatinib, gefitinib, ibrutinib, imatinib, lapatinib, lenvatinib, mubritinib, nilotinib, panitumumab, pazopanib, pegaptanib, ponatinib, ranibizumab, regorafenib, ruxolitinib, sorafenib, sunitinib, su6656, tofacitinib, trastuzumab, vandetanib, vemurafenib, and the like), endothelin receptor antagonist (e.g. atrasentan, and the like), proteasome inhibitor (e.g., bortezomib, and the like), Hsp 90 inhibitor (e.g., 17-AAG, and the like), spironolactone, minoxidil, 11α-hydroxyprogesterone, bone resorption inhibiting/metastasis suppressing agent (e.g., zoledronic acid, alendronic acid, pamidronic acid, etidronic acid, ibandronic acid, clodronic acid) and the like.

Non-limiting examples of hormonal therapeutic agents include fosfestrol, diethylstylbestrol, chlorotrianisene, medroxyprogesterone acetate, megestrol acetate, chlormadinone acetate, cyproterone acetate, danazol, dienogest, asoprisnil, allylestrenol, gestrinone, nomegestrol, Tadenan, mepartricin, raloxifene, ormeloxifene, levormeloxifene, anti-estrogens (e.g., tamoxifen citrate, toremifene citrate, and the like), ER down-regulator (e.g., fulvestrant and the like), human menopausal gonadotrophin, follicle stimulating hormone, pill preparations, mepitiostane, testrolactone, aminoglutethimide, LH-RH agonists (e.g., goserelin acetate, buserelin, leuprorelin, and the like), droloxifene, epitiostanol, ethinylestradiol sulfonate, aromatase inhibitors (e.g., fadrozole hydrochloride, anastrozole, retrozole, exemestane, vorozole, formestane, and the like), anti-androgens (e.g., flutamide, bicartamide, nilutamide, and the like), 5α-reductase inhibitors (e.g., finasteride, dutasteride, epristeride, and the like), adrenocorticohormone drugs (e.g., dexamethasone, prednisolone, betamethasone, triamcinolone, and the like), androgen synthesis inhibitors (e.g., abiraterone, and the like), and retinoid and drugs that retard retinoid metabolism (e.g., liarozole, and the like), etc. and LH-RH agonists (e.g., goserelin acetate, buserelin, leuprorelin).

In another embodiment, the cancer therapy may include probiotic bacteria, natural substances and nutraceuticals (e.g., green tea epigallocatechin gallate (EGCG) and reservatrol), hormone therapy (e.g., Selective Androgen Receptor Modulators (SARMs) such as enobosam (ostarine, MK-2866, GTx-024), BMS-564,929, LGD-4033, AC-262, 356, JNJ-28330835, LGD-3303, S-40503 and S-23), anti-inflammatory agents (such as COX-2 inhibitors and non-steroidal anti-inflammatory drugs (NSAIDs) such as Celexicob (Celebrex), Vioxx, Meloxicam, ibuprofen, naproxen (Anaprox, Naprosyn), diclofenac (Cambia, Cataflam, Voltaren), etodolac (Lodine), fenoprofen (Nalfon), flurbiprofen (Ansaid) and oxaprozin (Daypro)), cholesterol-lowering drugs such as statins (e.g., atorvastatin, cerivatstatin, fluvastatin, lovastatin, mevastatin, pitavastatin, pravastatin, rosuvastatin, simvastatin etc.), Poly (ADP-ribose) polymerase (PARP) inhibitors such as iniparib (BSI 201), BMN-673, Olaparib (AZD-2281), Rucaparib (AG014699, PF-01367338), Veliparib (ABT-888), MK 4827, BGB-290 and 3-aminobenzamide, inhibitors of mammalian target of rapamycin (mTOR), PI3K and IGF1R, and retinoids.

In other embodiments, the at least one additional medication is a targeted drug. The term "targeted drug" as used herein refers to a therapeutic agent that blocks cancer cell growth by interfering specific "targeted" molecules which are required for tumor growth. See, Pasquetto above, which is hereby incorporated by reference. In one aspect, the targeted drug includes, without limitation, dasatnib, imatinib, nilotinib, bosutnib, lestaurtinib, ruxolitinib, crizotinib, vandetabib, cabozantinib, denileukin diftitox, everolimus, and temosirolimus, among others.

Other chemotherapeutic or anti-cancer agents include, for example, antineoplastic enzymes, topoisomerase inhibitors, biological response modifiers, growth inhibitors, hematopoetic growth factors, immune modulators, chemokines, cytokines (for example Interleukin 2, a granulocyte-macrophage colony stimulating factor (GM-CSF) or FLT3-ligand), cell migration blockers, and inhibitors of angiogenesis. Angiogenesis inhibitors include, but are not limited to, angiostatin, endostatin, thrombospondin, Interleukin-12, a tissue inhibitor of metalloproteinase 1, 2 and 3 (TIMP-1, TIMP-2, and T1MP-3) and as anti-VEGF.

In another aspect, the at least one additional medication may comprise inhibitors of vitamin D catabolism for example, inhibitors of the enzyme 24-hydroxylase. 24-hydroxylase reduces the levels of circulating levels of active forms of vitamin D to less active forms that excreted primarily by feces. Non-limiting examples of such inhibitors include soy isoflavone and genistein. Additional combinations, with which the compounds of formula (I) or (II) may be administered, include without being limited to, gemcitabine and nab-paclitaxel, and etoposide and cisplatin.

In another aspect, the at least one additional medication administered to a subject in combination with the compounds of formula (I) disclosed herein may comprise micro-RNA (miRNA), up-regulators or down-regulators of miRNA, or a combination thereof. Recent studies on miRNA profiling have revealed differential expression of miRNAs in breast carcinomas compared to their normal tissue counterparts. For example, miR-155, miR-21, miR-27, miR10b, are up-regulated and oncogenic in nature while miR-125 (a and b), miR145 and miR205 were down-regulated. Other studies have shown that loss of miR-140 expression results in increased breast cancer progression. As non-limiting examples, the compositions of the present invention may be administered to a subject in combination with miR-125a, miR-125b, miR-200, miR-145, miR-205, miR-146a, let-7a-d, miR-26a, miR-34, miR-31, miR-101, miR-200b, miR-335, miR-126, miR-206, miR-17-5p and miR-140 or up-regulators thereof. Other non-limiting examples, the compositions of the present invention may be administered to a subject in combination with down-regulators of miR-155, miR-10b, miR21, miR-27 and miR-520c, and miR-373.

In another aspect, the at least one additional medication administered to a subject in combination with the compounds of formula (I) disclosed herein may comprise, DNA methylation modulators. Aberrations in DNA methylation and in the proteins involved in DNA methylation are known to occur in cancer. Accordingly, the present invention encompasses compositions and treatment methods that comprise administering DNA methylation modulators in combination with the compounds of formula (I) of the present invention. In some embodiments, the DNA methylation modulator is a DNA methylation inhibitor. Examples of DNA methylation inhibitors include without limitation, 5-Azacytidine, 5-aza-2'-deoxycytidine, MG98, or a DNA methylation activator like S-Adenosylmethionine (SAM).

The non-drug therapy is exemplified by surgery, radiotherapy, gene therapy, thermotherapy, cryotherapy, laser cauterization, and the like, and any combinations thereof.

EXAMPLES

The following examples are provided for illustrative purposes only and not to limit the scope of the claims provided herein.

Example 1: Production of Cpd.11 Ms and of Main Cytotoxic Metabolites

Materials & Methods

Synthesis and Metabolization of Cpd.11 Ms

Starting compound 1 (3,4-difluorobenzaldehyde) was used to prepare the intermediate compound 2 (3-fluoro-4-(methylsulfonyl)benzaldehyde), Compound 3 (3-fluoro-4-(methylsulfonyl)benzoic acid), and Compound 4 (5-fluoro-4-(methylsulfonyl)-2-nitrobenzoic acid) in accordance to the process described in WO2014031012. Compounds 1 to 4 may be also obtained commercially. The acid chloride Compound 5 was obtained by suspending Compound 4 in dichloromethane and acetonitrile prior to the addition of DMF and of oxalyl chloride to provide a homogenous solution. After removing the solvents and excess oxalyl chloride, the resulting crude acid chloride Compound 5 was dissolved in dichloromethane and THF and cooled to −10° C. before adding a solution of 1-ethylpiperazine in dichloromethane. The reaction mixture was stirred at ambient temperature and the resulting precipitate was collected by filtration then dried to obtain the crude hydrochloride salt of Compound 6 ((4-ethylpiperazin-1-yl) (5-fluoro-4-(methylsulfonyl)-2-nitrophenyl) methanone) that was then suspended in ethyl acetate and treated with a saturated solution of sodium bicarbonate. The resulting aqueous phase was further extracted with ethyl acetate and the combined organic layers were dried over anhydrous sodium sulphate. The solvent was removed and the resulting solid was dissolved in dichloromethane and precipitated by the addition of diisopropyl ether. The precipitate was collected by filtration and dried to provide Compound 6 ((4-ethylpiperazin-1-yl) (5-fluoro-4-(methylsulfonyl)-2-nitrophenyl) methanone).

Compound 6 was dissolved in DMF and cooled to 0° C. before adding Lithium bromide. A viscous red solution containing some undissolved lithium bromide was formed. The reaction mixture was cooled to −5° C. and 1-Aziridine ethanol was added forming a paste. The reaction mixture was stirred until TLC (dichloromethane/methanol 24:1) indicated no starting material remained. Deionized water was added at 2.5° C., the resulting dark yellow solution was extracted with ethyl acetate, and the combined organic layers were dried over anhydrous sodium sulphate. The solvents were removed and the resulting yellow oil was further concentrated to remove remaining traces of DMF. The residue was dissolved in ethyl acetate, loaded onto a silica gel column and chromatographed by gradient elution using dichloromethane/methanol 65:1 and 24:1 to collect the by-products, and dichloromethane/methanol 19:1 to collect the desired product. The combined fractions containing the product were concentrated to provide Compound 7 (5-((2-bromoethyl) (2-hydroxyethyl)amino)-4-(methylsulfonyl)-2-nitrophenyl) (4-ethylpiperazin-1-yl) methanone, in the form of a yellow solid).

Compound 7 was dissolved in dichloromethane and cooled to −5° C. before adding Triethylamine and Methanesulfonic anhydride, the latter prior was dissolved in dichloromethane. The reaction mixture was treated with saturated solution of sodium bicarbonate and the aqueous phase was extracted with dichloromethane. The combined organic layers were dried with anhydrous sodium sulphate and concentrated. The residue was dissolved in ethyl acetate, loaded onto a silica gel column and chromatographed by gradient elution using ethyl acetate/methanol 32:1 and 19:1 to collect the by-products, and dichloromethane/methanol 19:1 to collect, combine, and concentrate the fractions containing Compound 11 (2-((2-bromoethyl) (5-(4-ethylpiperazine-1-carbonyl)-2-(methylsulfonyl)-4-nitrophenyl)amino)ethyl methanesulfonate, in the form of a yellow glassy solid). Compound 11 was dissolved in dichloromethane and methanol and cooled to 0°. Methanesulfonic acid was added forming a solution. The reaction mixture was stirred at 0° C. and allowed to warm to room temperature with stirring. After removing the solvents, the resulting yellow glassy solid was concentrated, obtaining Compound 11 Ms (4-(5-((2-bromoethyl) (2-((methylsulfonyl)oxy)ethyl)amino)-4-(methylsulfonyl)-2-nitrobenzoyl)-1-ethylpiperazin-1-ium methanesulfonate, in the form of a yellow powder).

The full conversion of starting materials or intermediates during the reactions, the purity, and the molecular weight of the resulting compounds listed above was confirmed by applying common analytical techniques such as TLC, 1H NMR, or HPLC.

Synthesis of Cpd.11 Deuterated Variant Cpd.11 Ms-d8

Boc-protection of commercially available deuterated piperazine (Pip-d8) was performed following a literature procedure. Briefly, Pip-d8 (2.00 g, 21.23 mmol) was dissolved in methanol (80 mL) to give a colourless solution. TFA (1.626 mL, 21.23 mmol) was added in one portion and the mixture was stirred for 15 minutes upon which a thin white suspension formed. The reaction temperature increased from 20° C. to 23° C. Subsequently water (80 mL) was added upon which the mixture turned into a clear colorless solution, the reaction temperature increased further to 28° C. The mixture was stirred for 30 minutes while cooling back to room temperature. A solution of di-tert-butyl dicarbonate (4.63 g, 21.23 mmol) and iodine (0.109 mL, 2.123 mmol) in methanol (160 mL) was added dropwise to the mixture within 2 hours. The reaction was continued overnight at room temperature forming, according to GCMS analysis a mixture of Boc-Pip-d8 (83.9%) and di-Boc-Pip-d8 side product (14.6%) di-Boc side-product were formed. The reaction mixture, a dark red to brown clear solution, was concentrated in vacuo to remove methanol and iodine. This afforded a slightly yellow suspension (~50 mL). To the stirred suspension was added an aqueous solution of sodium hydroxide (20% (w/v), 7 mL) until a pH of 11-12 was reached. The suspension was filtered through a P3 glass filter, the residue (presumably containing the di-Boc side-product) was washed with an aqueous solution of sodium hydroxide (6% (w/v), 10 mL). The filtrate was extracted with ethyl acetate (3×100 mL) and the combined organic phases were washed with brine (60 mL), dried with sodium sulfate and concentrated in vacuo affording 3.43 g of Boc-Pip-d8 as a colourless clear oil, which crystallized upon standing. GCMS analysis showed a purity of 99.6% of Boc-Pip-d8 preparation.

The preparation of deuterated 1-ethylpiperazine (Boc-Epip-d8) was performed using Boc-Pip-d8 (3.44 g, 17.70 mmol) that was mixed in a 1-necked flask (100 mL) with acetonitrile (33 mL) to give a turbid solution. The mixture was cooled on an ice bath for 15 minutes prior to adding DIPEA (4.63 mL, 1.5 eq.) and 1-bromoethane (1.98 mL, 1.5 eq. mmol). The cooling bath was removed and the mixture was stirred at room temperature overnight. GCMS analyses showed complete conversion and 97.3 area % formation of Boc-Epip-d8. The reaction mixture (turbid solution) was poured into a stirred mixture of brine (150 mL) and ethyl acetate (50 mL). Water (10 mL) was added to the stirred mixture until a clear 2-phase system was formed. Layers were separated and the organic layer was washed with brine (50 mL), dried with sodium sulfate and concentrated to dryness affording 3.61 g crude Boc-EPip-d8 as a cloudy, very pale-yellow oil. This material was diluted with heptane/ethyl acetate (1:1, 5 mL) and the resulting suspension was filtered. The filtrate was purified by Reveleris® flash chromatography (80 g silica; 20-100% EtOAc in heptane). All product-containing fractions were collected and concentrated to dryness and chased with DCM providing 3.04 g Boc-EPip-d8 as a clear colorless oil. GCMS analysis showed a purity of >99% and 1H-NMR analysis confirmed structure.

The subsequent Boc-deprotection to obtain EPip-d8 was performed by dissolving Boc-EPip-d8 (3.04 g, 13.67 mmol) in dichloromethane (90 mL) and then adding dropwise trifluoroacetic acid (15 mL, 14 eq.) over a 5-minute period under water-bath cooling, keeping the reaction temperature below 20° C. The reaction was continued at room temperature for 2 hours. GCMS analyses showed full conversion towards the desired product. The mixture was concentrated in vacuo and chased with dichloromethane (3×5 mL) to afford 9.65 g of the crude TFA salt of Boc-EPip-d8 as a colorless oil. Of this crude material 1 g was freebased with saturated aqueous potassium carbonate solution (30 mL) and dichloromethane (2×30 mL). Additional extraction with dichloromethane/methanol (9:1; 3×20 mL) afforded 210 mg crude free-base after drying with sodium sulfate and concentration in vacuo. This material was a colorless oil with a considerate amount of solids present (purity of >98% by GCMS analysis). The remainder of the crude TFA salt of Boc-EPip-d8 (8.65 g) was triturated in MTBE (150 ml) overnight affording 3.95 g of TFA salt Boc-EPip-d8 as a white powder after filtration and drying. According to 1H-NMR analyses this material was the di-TFA salt and of high purity. This isolated yield corrected for solvents and loss of material for free-basing was 92%, 500 mg of this pure Boc-EPip-d8. 2TFA was freebased with saturated aqueous sodium carbonate solution (20 mL) and dichloromethane (3×30 mL) afforded 140 mg free-base Epip-d8 after drying with sodium sulfate and concentration in vacuo (T<40° C., p>150 mbar). This material was a colorless clear oil with no solids present. GCMS analyses showed a purity of >98% and 1H-NMR analysis was in agreement with structure. EPip-d8 was then used in the reaction based on Compound 5 described above, generating the deuterated intermediate Cpd.6-d8, and consequently reacted to generate Cpd.7-d8, Cpd.11-d8, and Cpd.11 Ms-d8.

Synthesis of Cpd.11 Metabolites Cpd.11c, Cpd.11d and their Deuterated Variants

Cpd.11 Ms (0.50 g) was free-based by dissolving in water (5 mL), addition of dichloromethane (10 mL) and washing with saturated $NaHCO_3$ solution. The aqueous phase was back extracted and the combined organic layer was concentrated in vacuo to produce Cpd.11 free base (0.470 g; purity by HPLC: 96.6%).

Cpd.11c is produced by dissolved free base Cpd.11 in EtOH (7.5 mL and THF (5 mL), degassed and Pd/C (10 wt %; Sigma Aldrich, 6 mol %) was added. The mixture was stirred under hydrogen atmosphere (balloon) for 2.5 hours. 63% of the desired product was formed. The reaction was stopped because over reduction was observed. The mixture was filtered off over a 0.45 μm filter, and concentrated in vacuo to produce Cpd.11c free base as a yellow oil (0.485 g, 95% yield).

Cpd.11d is produced by nitro-reduction using Pt/C catalyzed hydrogenation. A glass vial was loaded with a magnetic stirrer, free base Cpd.11 (100 mg, 0.17 mmol), ethyl acetate (1 ml) and platinum on carbon (5 wt %, 80 mg, 0.12 eq.). The vial was closed with a punctured septum and placed in a parallel autoclave and stirred overnight at 40 psi of hydrogen pressure at 20° C. The reaction mixture was subsequently filtered over a small pad of kieselguhr, which was rinsed with EtOAc (2 mL). The filtrated was concentrated to dryness affording 60 mg crude Cpd.11d as a free base. HPLC and LCMS analyses showed a purity of 87%. Some impurities were eliminated by prep-LCMS (eluent: MeCN/water ammonium bicarbonate). The product containing fractions were extracted with dichloromethane, dried with sodium sulfate and concentrated to dryness (T<30° C.). After a further nitro-reduction by Pt/C catalyzed hydrogenation, the product was then repurified by Prep-SFC (eluent: CO2/Methanol+20 mM Ammonia) affording Cpd.11d as an off-white foam. HPLC analyses showed a purity of 98.9%.

The deuterated variants Cpd.11c-d8 and Cpd.11d-d8 were produced using Cpd.11dMs-d8 and the protocols described above for Cpd.11c and Cpd.11d.

Results

The preclinical studies performed using compounds disclosed in WO2014031012 identified series of nitrophenyl mustard prodrugs that were synthesized and characterized by HPLC, MS, NMR and elemental analysis. However, this document discloses neither the most appropriate compounds for medical use nor the most appropriate medical uses. Indeed, the more extensive preclinical validation also needs establishing a process for the synthesis of compounds that allows obtaining the desired compounds in the quantity and quality that are sufficient for their development as HAPs useful for treating cancer.

Among 4-alkylsulfone prodrugs of Formula (I) in WO2014031012 (in particular among those shown in FIG. 1A), specific compounds of the present invention are the most promising with respect to aqueous solubility, tolerated dose, and/or bioavailability. WO2014031012 discloses some general protocols for the synthesis of symmetrical and unsymmetrical haloalkanesulfonate mustards of Formula (I). In order to pursue a more extensive characterization of the cancer cells more sensitive to the cytotoxic properties of such selected compounds, the compound 11 (Cpd.11, identified in WO2014031012 as compound 311) has been selected as reference compound for defining the preferred salt (being the methanesulfonate salt, named Cpd.11 Ms) and an improved process for production. This process, summarized in FIG. 1B together with the related intermediate products, can be generalized to provide unsymmetrical haloalkanesulfonate mustards of Formula I in sufficient amounts for testing the compounds in relevant cell- and animal-based cancer models and evaluating the specific uses for further validation in preclinical assays.

The biological activities of prodrugs in general, and of haloalkanesulfonate mustards of formula (I) in particular, result from their metabolization by human enzymes under hypoxic conditions into cytotoxic compounds. However, specific steps in this process may be associated to normoxic or oxygen-independent conditions. As exemplified in the process based on Cpd.11 structure that is shown in FIG. 1C, alternative structures (Cpd.11a, Cpd.11b, Cpd.11c, and Cpd.11d, having variable but in general short half-life in vivo) may result from the oxidative status and the interaction of Cpd.11 with human enzymes that are variably expressed and active in normal tissues, normoxic regions of tumor, and anoxic regions of tumors. In the latter ones, the absence of oxygen triggers the key transition from Cpd.11a to Cpd.11b allows generating cytotoxic compounds that would then exert their activity in such location and may contribute to the destruction of whole tumor by the organism, alone or in association to immunological anti-cancer response, or treatments such as radiotherapy, chemotherapy, and/or other drugs.

Figure 2:
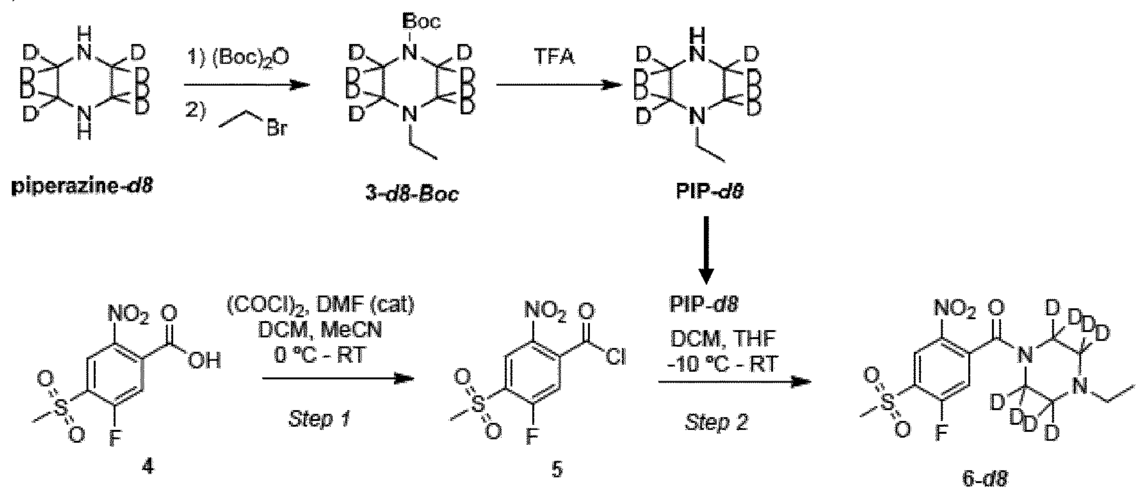
FIG. 2: synthesis of specific Cpd.11c and Cpd. 11d metabolites and of their deuterated variants. The synthesis process of the reference unsymmetrical haloalkanesulfonate mustard of formula I named Cpd.11 Ms that is described in FIG. 1B can be adapted to produce the deuterated form Cpd.11 Ms-d8 in which the 8 hydrogen atoms in the piperazine ring are all deuterated by substituting 1-ethylpiperazine with corresponding deuterated version in the reaction for producing compound 6 from compound 5, all later reactions remaining the same (A). Original mesylate salt (Cpd.11 Ms) and the deuterated mesylated salt (Cpd.11 Ms-d8) can be reduced to produce the metabolites Cpd.11c and Cpd.11d, as such or in their corresponding deuterated forms, Cpd.11c-d8 and Cpd.11d-d8 (B-E).
Figure 2:
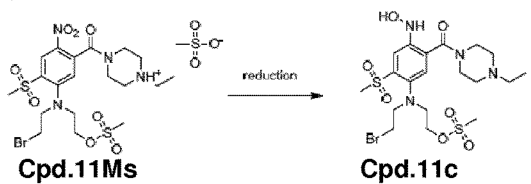
Figure 2:
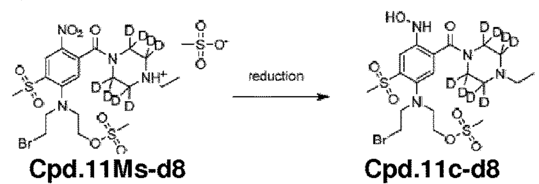
Figure 2:
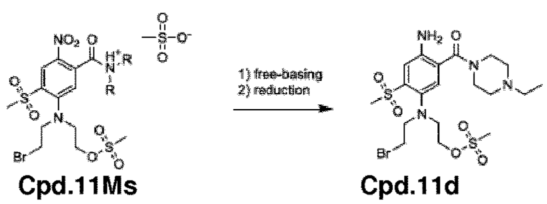
Figure 2:
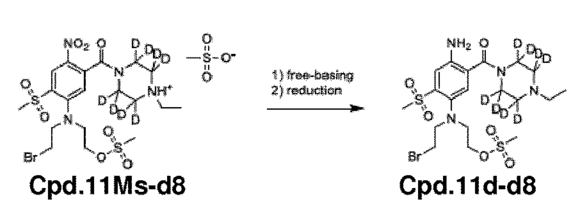

Additional compounds of Formula (I) can be prepared as synthetic compounds corresponding to the metabolites that generated in vivo or as deuterated variants in which deuterium atoms substitutes the hydrogen atoms in the piperazine ring (FIG. 2). These variants may be used, aside for their therapeutic activities, for evaluating the localization, metabolization, accumulation and/or the biological activities of compounds of Formula (I).

Example 2: In Vitro Validation of Cpd.11 Ms and Cpd.11c, and Cpd.11d as Anti-Cancer Agents Active in Hypoxic Conditions Cancer Cell Lines-Based Assay Using Cpd.11 Ms The tested cancer cell lines that were used for in vitro and/or in vivo studies with shown results are available through ATCC or through DSMZ (Leibniz-Institut—Deutsche Sammlung von Mikroorganismen und Zellkulturen GmbH) and are grouped by type of cancer, au summarized in Table I.

TABLE I

| Name | Provider | Catalog No. | Subtype |
|---|---|---|---|
| Breast cancer cell lines | | | |
| BT-474 | DSMZ | ACC-64 | HER2+ER+PR+ |
| EFM-19 | DSMZ | ACC 231 | Luminal A |
| HCC1937 | DSMZ | ACC-513 | TNB |
| HS-578T | DSMZ | ACC 781 | TNB |
| MDA-MB-231 | DSMZ | ACC-732 | TNB |
| MDA-MB-453 | DSMZ | ACC-65 | TNB |
| MDA-MB-436 | ATCC | HTB-130 | TNB |
| MDA-MB-468 | DSMZ | ACC-738 | TNB |
| SK-BR-3 | DSMZ | ACC-736 | HER2+ |
| T47D | DSMZ | ACC-739 | ER+ PR+ |
| Lung cancer cell lines | | | |
| A-427 | DSMZ | ACC 234 | NSCLC |
| A549 | DSMZ | ACC-107 | NSCLC |
| DMS114 | ATCC | ATCC-CRL-2066 | SCLC |
| NCI-H69 | ATCC | ATCC-HTB-119 | SCLC |
| NCI-H1299 | ATCC | ATCC-CRL-5803 | NSCLC |
| NCI-H1650 | ATCC | ATCC-CRL-5883 | NSCLC |
| NCI-H1975 | ATCC | ATCC-CRL-5908 | NSCLC |
| NCI-H460 | DSMZ | ACC-737 | NSCLC |
| Pancreatic cancer cell lines | | | |
| BxPC-3 | ATCC | CRL1687 | Exocrine |
| Capan-1 | DSMZ | ACC-244 | Exocrine |
| Hs766t | ATCC | HTB-134 | Exocrine |
| MiaPaCa-2 | DSMZ | ACC-733 | Exocrine |
| Panc-1 | DSMZ | ACC-783 | Exocrine |
| SW1990 | ATCC | CRL2172 | Exocrine |

Other cancer cell lines that were tested only for in vitro anoxia-based cytotoxicity, confirming Cpd.11d sensitivity, covered these and other cancer subtypes: for breast cancer, EFM-192A (Luminal B), EVSA-T (PR+/ER), and JIMT-1 (HER2+); for lung cancer several other NSCLC or SCLC cancer cell lines; for pancreatic cancer, carcinoma (DAN-G, YAPC), adenocarcinoma (HUP-T4). All cell lines were maintained in cell culture flasks, using complete medium according to provider's instructions.

Cell-Based Assay Using Cpd.11 Ms, Cpd.11c, and Cpd.11d

The $IC_{50}$ values were obtained using the resazurin-based potency assay under anoxic (<0.01% O2) and/or normoxic conditions (21% O2). The hypoxia cytotoxicity ratio (HCR) is calculated as the ratio of $IC_{50}$ value under anoxia to the $IC_{50}$ value under normoxia ($HCR=IC_{50}$ normoxia/$IC_{50}$ anoxia).

For anoxic condition, the complete medium for each cell line (25 ml in a T25 or 80 ml in a T80) was equilibrated in the anoxic chamber 48 h before use to allow an as large as possible interchange between media and atmosphere, agitating the flask once a day and just before use. The 96-well plates for cell seeding and the 96-well plates for preparation of a mother plate containing the compound to be tested (e.g. Cpd.11 Ms) at appropriate concentrations as well as disposable reagent reservoirs and pipet tips that are required for cell seeding under anoxic conditions were placed in anoxia at least 72 h before use. The mother plate for treatment of the cells under anoxia was prepared with anoxic medium and in anoxia pre-incubated plastics, the mother plate for treatment of the cells in normoxia was prepared with normoxic medium in a standard cell culture hood.

Cell seeding was performed starting from a cell suspension (70% confluent flasks of cells). Appropriate cell numbers/volumes were used at the pre-determined cell density (typically 100 µl/well) as determined by performing a growth curve experiment were calculated. For anoxic conditions, the appropriate number of cells was transferred to the anoxic chamber and diluted to the appropriate cell concentration in anoxic complete medium. The cells were allowed to adhere for 2 hours in the anoxic chamber at 37° C. In normoxic conditions, usual cell seeding and complete medium protocols were used (in a volume of 100 µl/well in 96-well plates). The cells were allowed to adhere for 2 hours at 37° C. in a regular cell culture CO2 incubator. In both conditions, the remaining empty wells in 96-well plates were filled with 200 µl anoxic or normoxic medium to prevent evaporation.

Fresh Cpd.11 Ms stock solution was thawed just before the experiment and shielded from the light. A 96-well microtiter plate was filled with 176.4 µl of complete normoxic (RT) or anoxic medium in the first column and 120 µl of complete normoxic or anoxic medium with 2% DMSO for the other columns of wells. 3.6 µl per well of the compound stock solution (Cpd.11, Cpd.11 Ms, Cpd.11c, or Cpd.11d; 150 mM) was added to the first column. The solution of the first column was pipetted up and down and 60 µl was transferred to the second column to perform 1/3 serial dilutions pipetting up and down 3 times between each transfer. This was repeated until the 11th column. No Cpd.11 Ms was added to the 12th column. The plate was prepared no longer than 30 minutes before use and protected from direct light exposure. Two hours after seeding the cells, 100 µl of the mother plate was added to each well and plates remained for 4 h in the anoxic chamber or in cell culture incubator at 37° C. After 4 h, the plate in the anoxic chamber was transferred to normoxia. Visual inspection of all plates (few random wells per plate) under microscope was performed and medium was removed from all plates by aspiration. Cells were washed once with 200 µl PBS (RT) and 200 µl of fresh normoxic complete medium (RT) was added to each well (including all wells without cells). All plates were incubated for 96 hours in normoxia at 37° C. in a standard cell culture incubator.

For the cell viability assay, the resazurin final working solution was prepared freshly by diluting the resazurin stock solution (0.1 mg/ml) 1/10 in complete medium (RT) of the respective cell lines to obtain a final concentration of 0.01 mg/ml resazurin. After 96 hours incubation in normoxia, a visual inspection of all the plates (few random wells per plate) was performed under the microscope and the medium in each well was removed by aspiration. Resazurin final working solution (200 µl) was added per well (including all wells without cells) and cells were incubated for 2 h at 37° C. in a CO2 incubator. The plate reading was performed by using the TECAN fluorescence reader, measuring fluorescence at excitation 535/35 nm and emission 610/20 nm. RFU (Relative Fluorescence Unit) values were calculated as an average of RFU values obtained compared with wells without cells with the same medium per plate to obtain a blank value for each plate (to be subtracted from the RFU value obtained for each well). Statistical data analysis was performed using Graphpad prism.

An in vitro ATP-based potency commercial assay (Cell-Titer-Glo 2.0 luminescent cell viability; Promega) was used to assess compound efficacy in a panel of 51 human cancer cell lines including breast cancer cell lines, pancreatic cancer cell lines and lung cancer cell lines that were suitable for IC50 determination under normoxic and anoxic conditions.

Results

A first type of validation of compounds of Formula (I) was pursued in a panel of cancer cell lines where the cytotoxic activities in hypoxic or normoxic conditions had been established, in particular by calculating the median inhibitory concentrations ($IC_{50}$) for normoxia and hypoxia, and a hypoxia cytotoxicity ratio (HCR) reflecting the hypoxia-selective cell killing, as also used for other HAPs such as TH-302 (Meng F et al., 2012). The data for a selection of cancer cell lines that were tested with Cpd.11 Ms are summarized in Table II.

TABLE II

| Cancer type | Cell line Name | $IC_{50}$Average for Cpd.11Ms NRX (SD) | ANX (SD) | Average of HCR (SD) |
|---|---|---|---|---|
| Pancreas | BxPC-3 | >1500.0 μM (390.9) | 68.2 μM (3.7) | 22.7 (4.2) |
| | PANC-1 | 1042.4 μM (95.7) | 43.6 μM (5.9) | 24.0 (1.0) |
| Lung | NCI-H1650 | 1246.3 μM (221.4) | 45.1 μM (9.6), | 28.2 (5.4) |
| | NCI-H1975 | 1144.8 μM (172.8) | 28.7 μM (2.6), | 52.6 (36.4) |
| | DMS114 | 563.6 μM (27.1) | 6.2 μM (0.7), | 96.3 (26.2) |
| Breast | BT-474 | >1500.0 μM (145.5) | 14.8 μM (2.0) | 102.6 (15.2) |
| | HCC1937 | 1451.3 μM (416.4) | 53.1 μM (3.5), | 28.8 (8.3) |
| | MDA-MB-231 | 1247.7 μM (337.0) | 121.1 μM (5.0) | 10.4 (3.0) |

Figure 3:
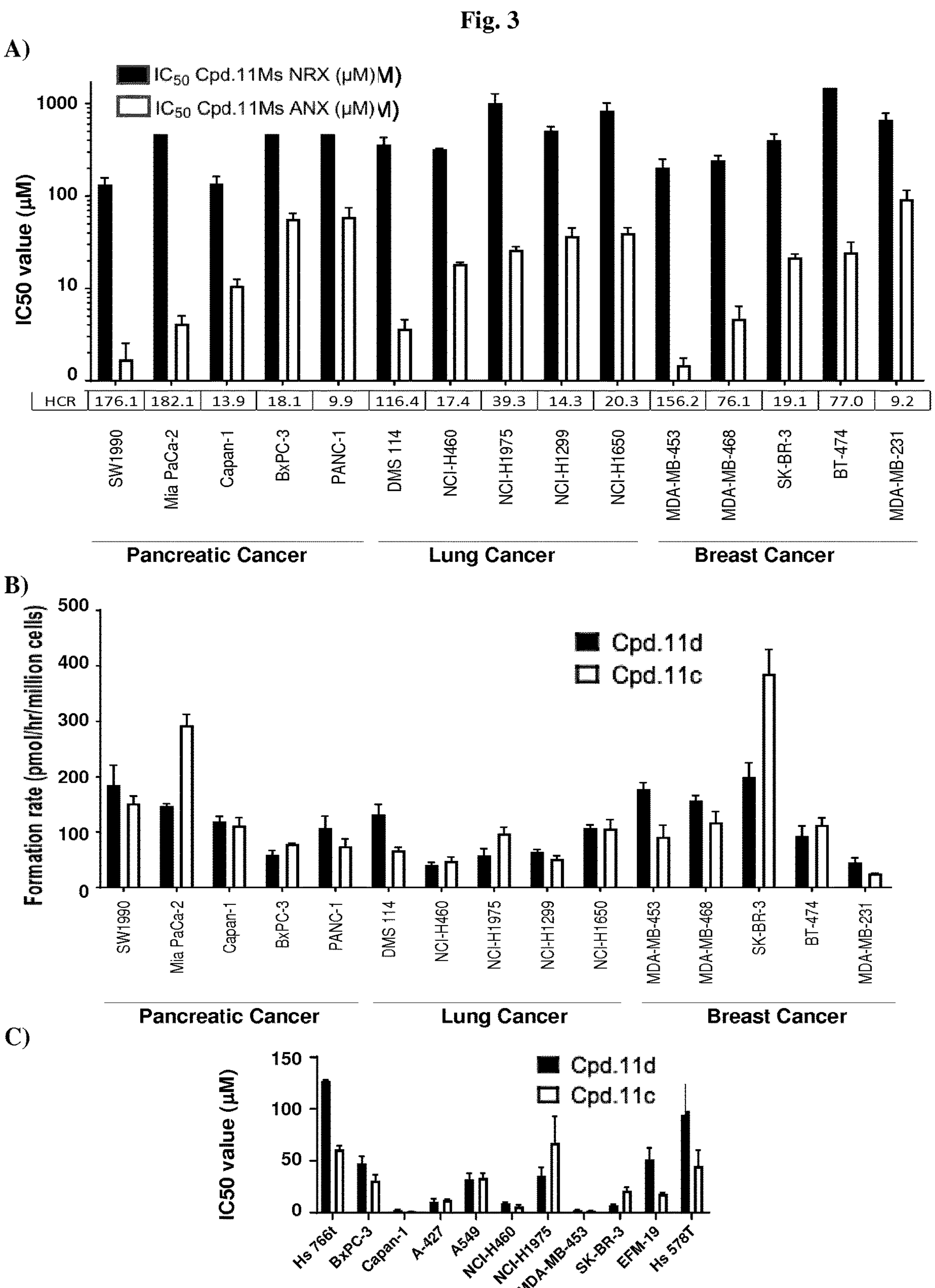
FIG. 3: cytotoxicity of Cpd.11 Ms and metabolites in normoxic and anoxic conditions in a panel of human cancer cell lines. Five cell lines, representative for each relevant cancer type, have been exposed to Cpd.11 Ms (4 hour drug exposure) in either normoxic (NRX) or anoxic (ANX) conditions and related $IC_{50}$ and HCR values have been calculated using an in vitro ATP-based potency assay, showing the anoxia-specific cytotoxicity of Cpd.11 Ms (A). The same panel of cell lines has been used to calculate the formation rate of Cpd.11c and Cpd.11d metabolites (B). A panel of human cell lines isolated from lung cancer (A-427, A459, NCI-460, NCI-H1975), pancreatic cancer (Hs 766T, BxPC-3, Capan-1), and breast cancer (MDA-MB-453, SK-BR-3, EFM-19, Hs578t) has been exposed to synthetic version of Cpd.11c and Cpd.11d metabolites, that present cytotoxic properties also in normoxic conditions (C). The average plating efficiency in the drug-free control wells was 43% under normoxic and 30% under anoxic conditions.

Averages are derived from at least 2 independent experiments
HCR = hypoxic cytotoxic ratio
NRX = normoxia
ANX = anoxia
SD = Standard Deviation The Cpd.11 Ms cytotoxic properties were validated in cancer cell lines that are isolated from cancers presenting different molecular features: exocrine pancreatic adenocarcinomas (for BxPC-3 and PANC-1), non-small cell (for NCI-H1650 and NCI-H1975) and small cell (for DMS114) lung cancer, HER2-positive (for BT-474), Basal like (for HCC1937) and mesenchymal-like (for MDA-MB-231) breast cancer cells. Additional data were generated using another assay (ATP-based potency assay) for a panel of breast cancer, lung cancer, and pancreatic cancer cell lines, obtaining $IC_{50}$ and HCR values confirming the anoxia-based dependency and specificity of such compound cytotoxicity (FIG. 3A).

This assay may allow validating either selected compounds among symmetrical and unsymmetrical haloalkanesulfonate mustards of Formula (I) and/or, depending on the choice of the cancer cell lines, other types or sub-types that are specifically sensitive to their cytotoxic derivatives (such as the ones that are exemplified for Cpd.11 Ms in FIG. 1C) in connection to tumor-specific hypoxic conditions. For instance, Cpd.11 Ms becomes biologically available as Cpd.11 after systemic administration and may be transformed into the oxygen-sensing intermediate Cpd.11a by one-electron reductases. This intermediate, when produced under hypoxic conditions (like those found in specific regions of tumours), may be further transformed into the oxygen-insensitive nitroso derivatives Cpd.11b and then rapidly, by oxygen-independent reductases, into the hydroxylamine cytotoxin Cpd.11c and amine cytotoxin Cpd.11d being biologically active against cancer cells in both hypoxic regions and redistribution or diffusion of the cytotoxic metabolites to neighboring cells upon activation (by-stander effect). Indeed, the same panel of cancer cell lines shows a strong and rapid ratio of conversion of Cpd.11 Ms into the hydroxylamine cytotoxin Cpd.11c and amine cytotoxin Cpd.11d (FIG. 3B), both confirmed as being cytotoxic against a panel of cancer cell lines when prepared by chemical synthesis and then directly tested on such cell lines in normoxic conditions (FIG. 3C).

If sensitivity to Cpd.11 Ms varied across cell lines, it was anyway consistently much greater in hypoxia, obtaining values for hypoxic cytotoxic ratio of 10 or more. These evidences can be confirmed in additional cancer cell lines growing either monolayers or forming spheroids, wherein hypoxic conditions and drug effects or metabolization can be evaluated in further details using microscopy, fluorescent probes, and or antibodies.

Example 3: Efficacy of Cpd.11 Ms in Animal Models for Lung, Pancreatic, and Breast Cancer Materials & Methods Animal Models All animal models were established as xenograft model in BALB/c Nude Mice (6-8 weeks old, 17-23 grams, maintained in standard conditions and diet), following approved IACUC (Institutional Animal Care and Use Committees) protocols. Cpd.11 Ms was formulated using 2% dimethyl sulfoxide (DMSO in water for injection, starting from a Cpd.11 Ms main preparation (100-60 mg/ml in 2% DMSO in water for injection).

After tumor cell inoculation, the animals were checked daily for morbidity and mortality. Before commencement of treatment all animals were weighed and the tumor volumes were measured using a caliper. The treatments were started when the mean tumor size reached approx. 250 $mm^3$. Each treated/control group contained 10 mice that were randomly assigned and injected daily for 5 days. The date of tumor cell inoculation was denoted as day 0 (thus injections were performed at day 1, 2, 3, 4, and 5). At the time of routine monitoring, the animals were checked for any effects of tumor growth and treatments on normal behavior such as mobility, visual estimation of food and water consumption, body weight gain/loss (body weights were measured daily during the 5-day treatment and thrice weekly after treatment), eye/hair matting and any other abnormal effect. Death and observed clinical signs were recorded on the basis of the numbers of animals within each subset. Tumor volumes were measured daily during the 5-day treatment and thrice weekly after treatment in two dimensions using a caliper, and the volume was expressed in mm3 using the formula: V=0.5 a×b2 where a and b are the long and short diameters of the tumor, respectively. The entire procedures of dosing as well as tumor and body weight measurement were conducted in a Laminar Flow Cabinet. Individual mice were euthanized by cervical dislocation when the tumor size reached 1400-1600 mm3. The surrogate endpoint for survival was calculated and indicated as TVx4 (initial tumor volume times 4). Statistical analysis of difference in tumor volume among the groups was conducted at the end of experiment using Independent-Samples T Test. All data were analyzed in SPSS (Statistical Product and Service Solutions) version 18.0 (IBM, Armonk, NY, U.S.). P-values were rounded to three decimal places, with the exception that raw P-values less than 0.001 were stated as P<0.001. All tests were two-sided. P<0.05 was considered to be statistically significant.

For the MDA-MB-436 tumor (ATCC: HTB-130; Passage: P4) cells were maintained in vitro as a monolayer culture in L-15 medium supplemented with 10% heat inactivated fetal bovine serum at 37° C. in an atmosphere of 100% air. For NCI-H69 (ATCC: HTB-119; Passage: P3), tumor cells were maintained in vitro in RPMI1640 medium supplemented with 10% fetal bovine serum at 370C in an atmosphere of 5% CO2 in air. For PANC-1 (ATCC: CRL-1469; Passage: P2) tumor cells were maintained in vitro as a monolayer culture in DMEM medium supplemented with 10% heat inactivated fetal bovine serum at 370C in an atmosphere of 5% CO2 in air. The tumor cells were routinely sub-cultured twice weekly by trypsin-EDTA treatment. The cells growing in an exponential growth phase were harvested and counted for tumor inoculation. Each mouse was inoculated with 1×107 tumor cells (orthotopically at the right mammary fat pad for MDA-MB-436 model, or subcutaneously at the right flank region for both NCI-H69 model and PANC-1 model) in 0.1 ml of PBS mixed with Matrigel (1:1, Corning, #354234) for tumor development. These material & methods were adapted to other xenograft cancer cell models for specific human cancer cell lines that summarized in Table III below.

Evaluation of Hypoxic State and DNA Damage in Xenograft Cancer Models.

To evaluate the impact of Cpd.11 Ms treatment on the induction of DNA damage, histological analysis of pH2AX staining and investigated colocalization of pH2AX and pimonidazole staining was performed in the small cell lung cancer model, DMS 114. DNA damage was assessed at 6 hours post a single administration of Cpd.11 Ms at 600 mg/kg. Pimonidazole Hydrochloride and pH2AX (Histone H2A.X, Phospho S139) antibodies are commercially available (Anti-Pimonidazole Hydrochloride, HP FITC Mab-1, HPI Hypoxyprobe Inc; Anti-Histone H2A.X (Phospho S139) antibody [EP854 (2) Y] ChIP Grade, ab81299, Abcam). From each xenograft sample, 3 non-sequential, 5 μm section levels with 50 μm spacing between each level were obtained. From each level, two or three serial sections were produced and collected on two or three slides depending upon the staining required: i) H&E and Pimonidazole or ii) H&E, Pimonidazole and pH2AX. Sections were then dried overnight at ~37° C. prior to staining. The H&Es were performed on a Leica ST4040 staining platform using harris haematoxylin and 1% eosin. Following antigen retrieval and subsequent protein blocking, the pH2AX antibody was incubated on the study tissue sections at a concentration of 1:48000 for 60 minutes. Following quenching of endogenous Horse Radish Peroxidase (HRP) activity using 3% hydrogen peroxide (aqueous), binding of pH2AX was visualised using a polymer based HRP driven detection system and ImmPACT DAB chromogen giving a brown reaction product at the site of antibody binding. A haematoxylin nuclear counterstain was then applied to the tissue sections. The Pimonidazole (FITC conjugated) antibody was incubated on the study tissue sections at a concentration of 1:5000 for 60 minutes. Following quenching of endogenous Horse Radish Peroxidase (HRP) activity using 3% hydrogen peroxide (aqueous), binding of Pimonidazole was visualised using an HRP conjugated rabbit anti-FITC secondary antibody (HPI Hypoxyprobe Inc, anti-FITC-HRP) and ImmPACT DAB chromogen giving a brown reaction product at the site of antibody binding. A haematoxylin nuclear counterstain was then applied to the tissue sections. Other steps of the protocol were performed according to literature or instructions from manufacturers.

Results

The cell-based assays and overall knowledge of hypoxia in tumours suggested selecting a series of xenograft models for specifically validating the efficacy of Cpd.11 Ms in breast cancer, lung cancer, and pancreatic cancer. The results obtained in such models can be further translated in the definition of cancer (sub) types that are sensitive to the cytotoxic derivatives of symmetrical and unsymmetrical haloalkanesulfonate mustards of Formula (I).

Figure 4:
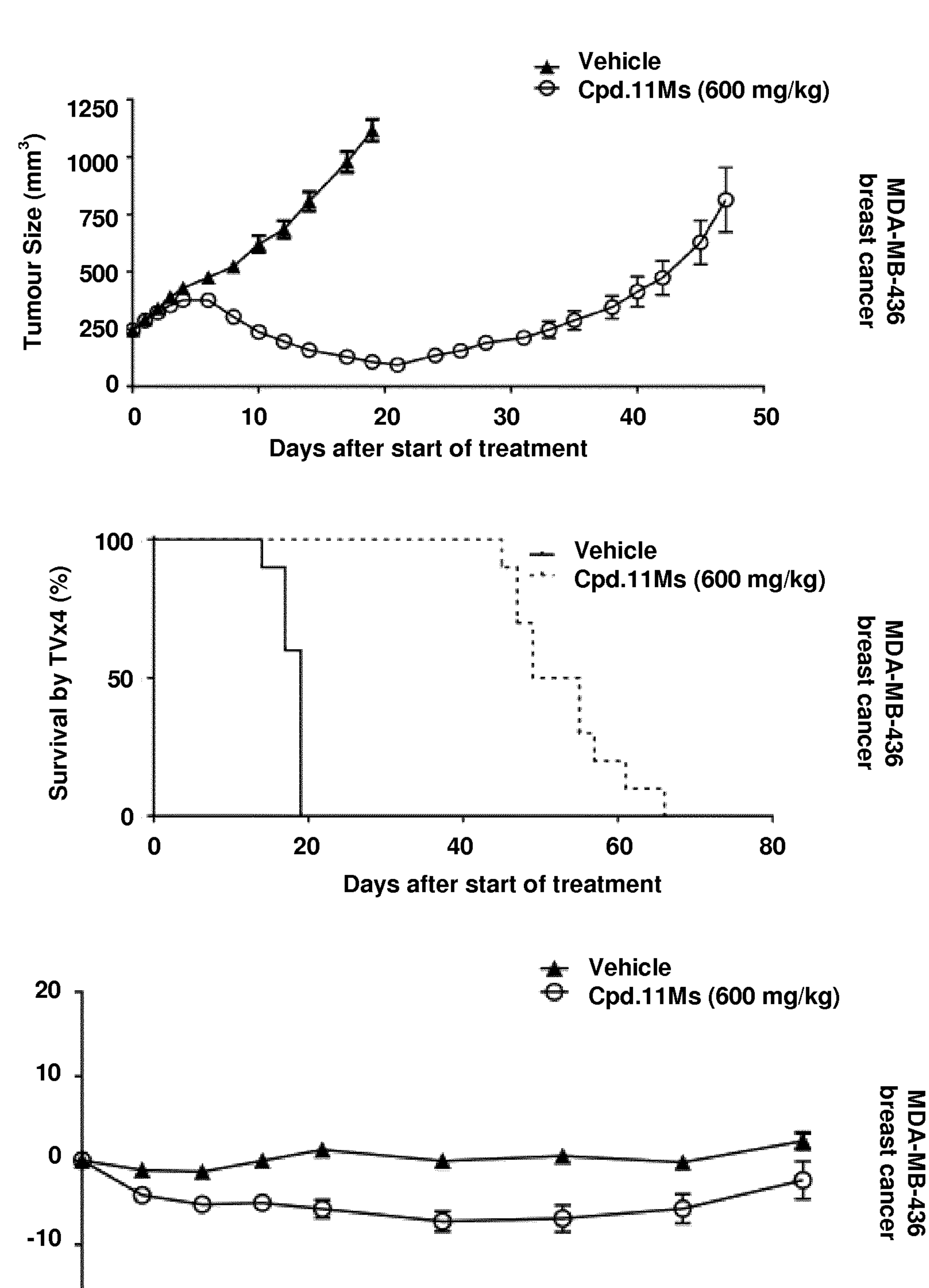
FIG. 4: efficacy of Cpd.11 Ms in a triple negative breast cancer xenograft model that has been established using the MDA-MB-436 breast cancer cell line. The strong effect of Cpd.11 Ms (administered intraperitoneally) on both tumour size (A) and animal survival (B; expressed as TVx4) is observed without major body weight loss.

Using MDA-MB-436 human cells (a relatively slow-growing tumour model for TNBC, Triple negative Breast Cancer, that is sensitive to alkylating agents or cisplatin), a strong response upon just a single treatment cycle with Cpd.11 Ms was observed with significant regression of the tumour and a corresponding median surrogate survival index that was more than double in the treated animals as compared to vehicle treated animals, in absence of effects on body weight (FIG. 4). Comparable efficacy and non-toxicity data were obtained using MDA-MB-231 breast cancer cell line in a further triple negative breast cancer xenograft model, a relatively fast-growing MDA-MB-231 TNBC tumour model that was rather insensitive to alkylating agents. A single treatment cycle induced a tumour growth rate reduction.

Figure 5:
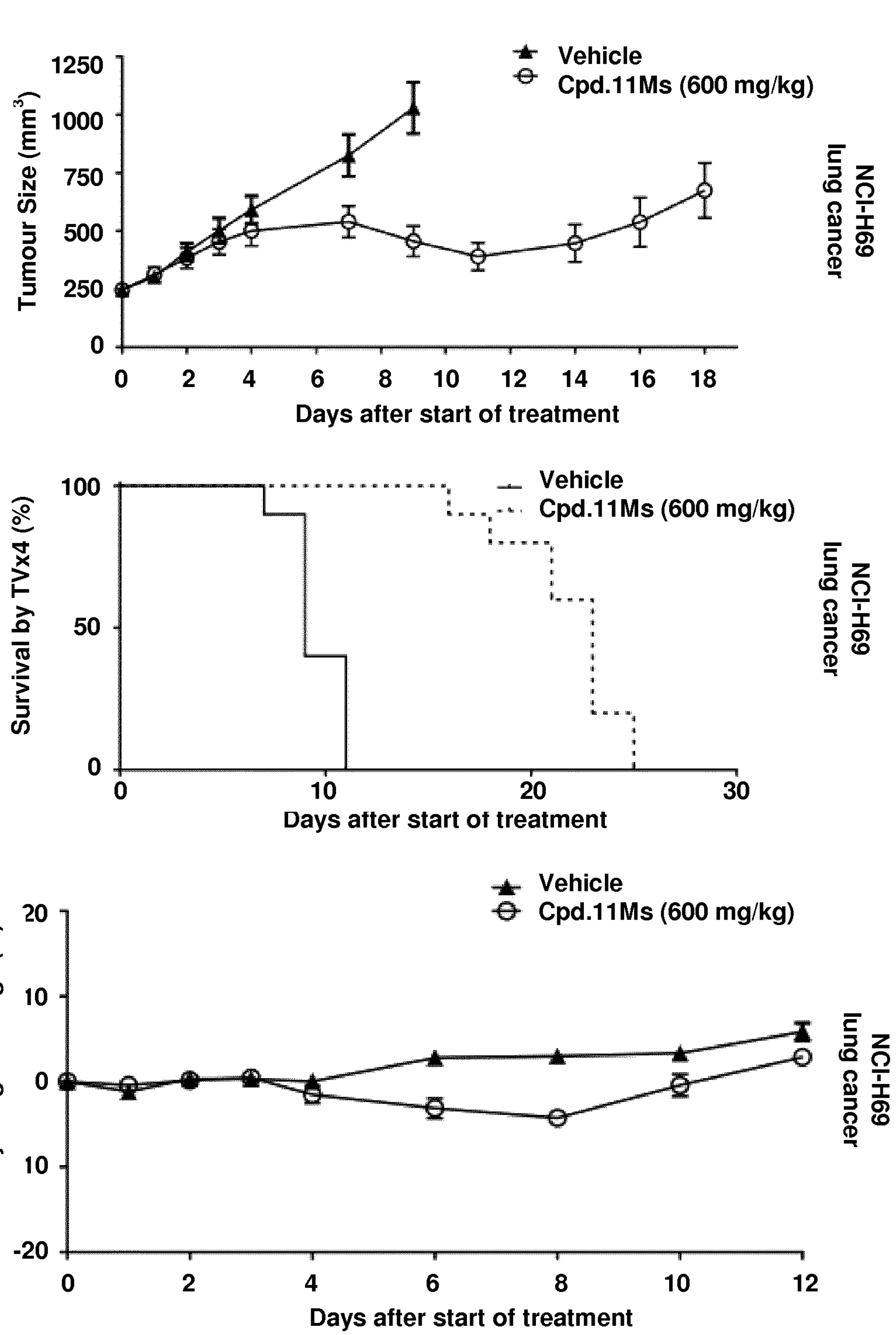
FIG. 5: efficacy of Cpd.11 Ms in the lung cancer xenograft model that has been established using NCI-H69 lung cancer line. As in FIG. 2, the strong effect of Cpd.11 Ms (administered intraperitoneally) on both tumour size (A) and animal survival (B; expressed as TVx4) is observed without major body weight loss (C).

Similarly, using NCI-H69 human cells (a relatively fast-growing tumour model for SCLC, Small Cell Lung Cancer, that is sensitive to alkylating agents), a similar strong response upon single treatment cycle was observed with a significant regression of the tumours after an initial growth rate reduction in comparison to the vehicle treated animals, in absence of effects on body weight. Median surrogate survival index of Cpd.11 Ms treated animals was also doubled in comparison to vehicle treated animals in this tumour model (FIG. 5). Comparable data were obtained using NCI-H1650 lung cancer cell line in a further, relatively fast-growing lung cancer xenograft model that was rather insensitive to alkylating agents including Cisplatin. A single treatment cycle with Cpd.11 Ms induced a significant effect on median surrogate survival index.

Figure 6:
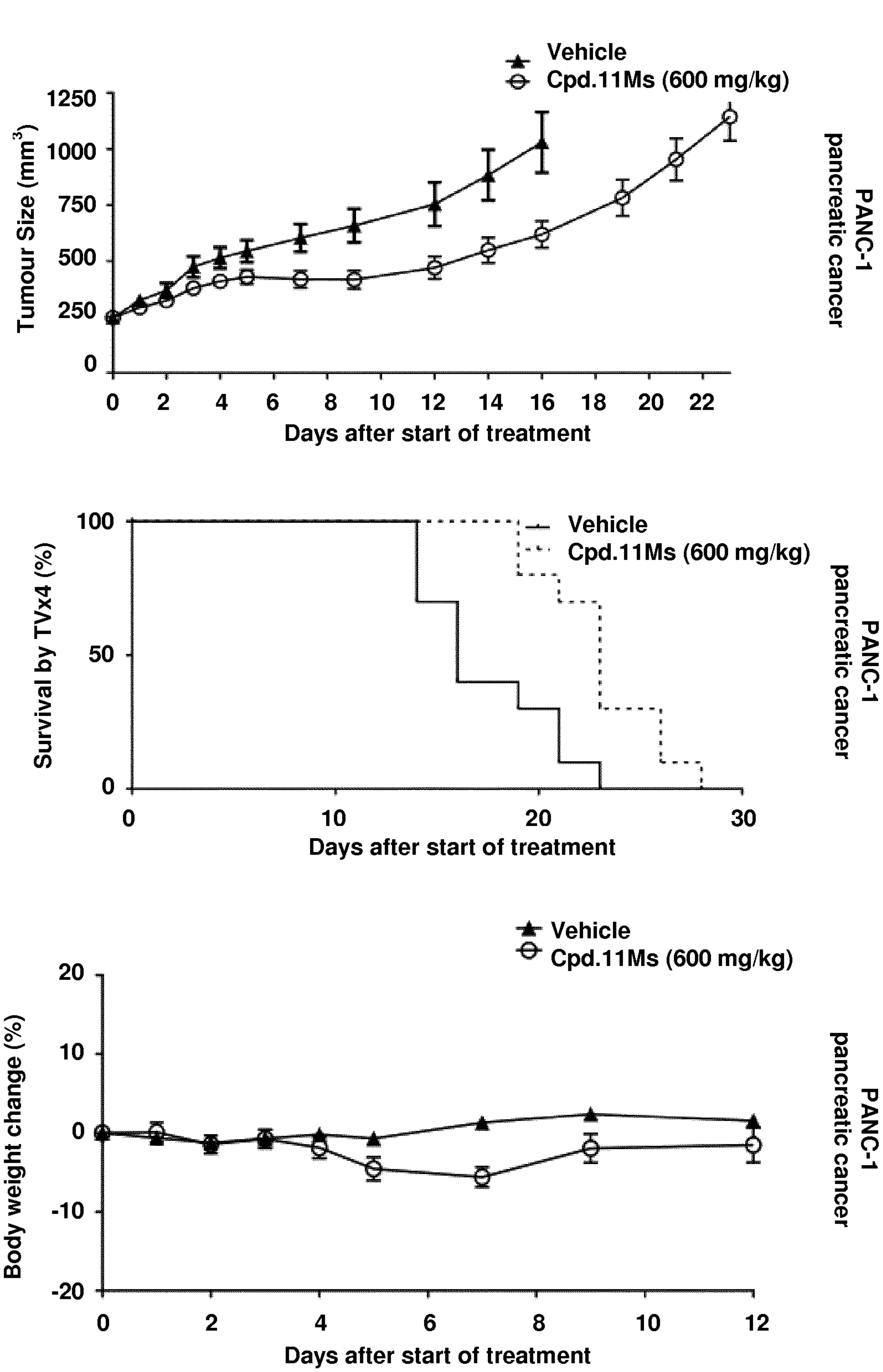
FIG. 6: efficacy of Cpd.11 Ms in the pancreatic cancer xenograft model that has been established using PANC-1 pancreatic cancer line. Effect of Cpd.11 Ms (administered intraperitoneally) on both tumour size (A) and animal survival (B; expressed as TVx4) is observed without major body weight loss (C).

Finally, using PANC-1 human cells (a relatively slow-growing tumour model for PDAC, pancreatic adenocarcinoma, that is poorly sensitive or insensitive to alkylating agents), a response upon single treatment cycle was observed, with a significant tumour growth retardation that results in a significant increase in median surrogate survival index (P=0.0018) by approx. 50% (FIG. 6).

Using the NCI-H69 human lung cancer models, the level of therapeutic response (in terms of tumor size and viability) was tested using alternative regimens with consecutive (at day 1, 2, 3, 4, and 5; at day 1, 2, 3) or non-consecutive (at day 1, 4, and 7) days of administration over one week or three weeks. This response appears correlated with number of consecutive administrations and repeated administration over 3 weeks results in longer term tumor control and can rescue later tumor escape or metastasis.

The analysis was extended to other xenograft models based on further breast, lung, or pancreas cancer cell lines (all sensitive to Cpd.11 Ms in anoxic cell culture conditions) but evaluating in parallel any relationship between the hypoxic state of the tumor induced by such cells and the observed anti-tumor effect. The main results are summarized in Table III.

TABLE III

| | Human cancer cell line | | Hypoxic status in tumor from | Cpd.11Ms treatment | |
|---|---|---|---|---|---|
| Cancer (subtype) | Name | Features | animal models | Dose, mg/kg (route) | Anti-tumor effect |
| Breast | MDA-MB-436 | Cisplatin- | Confirmed | 600 (IP) | Strong impact, |
| (TNBC) | MDA-MB-468 | sensitive | | 200-800 (IP) | clear regression |
| Lung | NCI-H69 | | | 600 (IP) | |
| (SCLC) | DMS 114 | Insensitive | | | Clear impact, |
| Lung | NCI-H1650 | to cisplatin | | | no regression |
| (NSCLC) | | | | | |
| Pancreas | PANC-1 | | | | |
| (PDAC) | MiaPaCa-2 | | Absent | | No impact |
| | SW1990 | Cisplatin- | | | |
| | | sensitive | | | |

Figure 7:
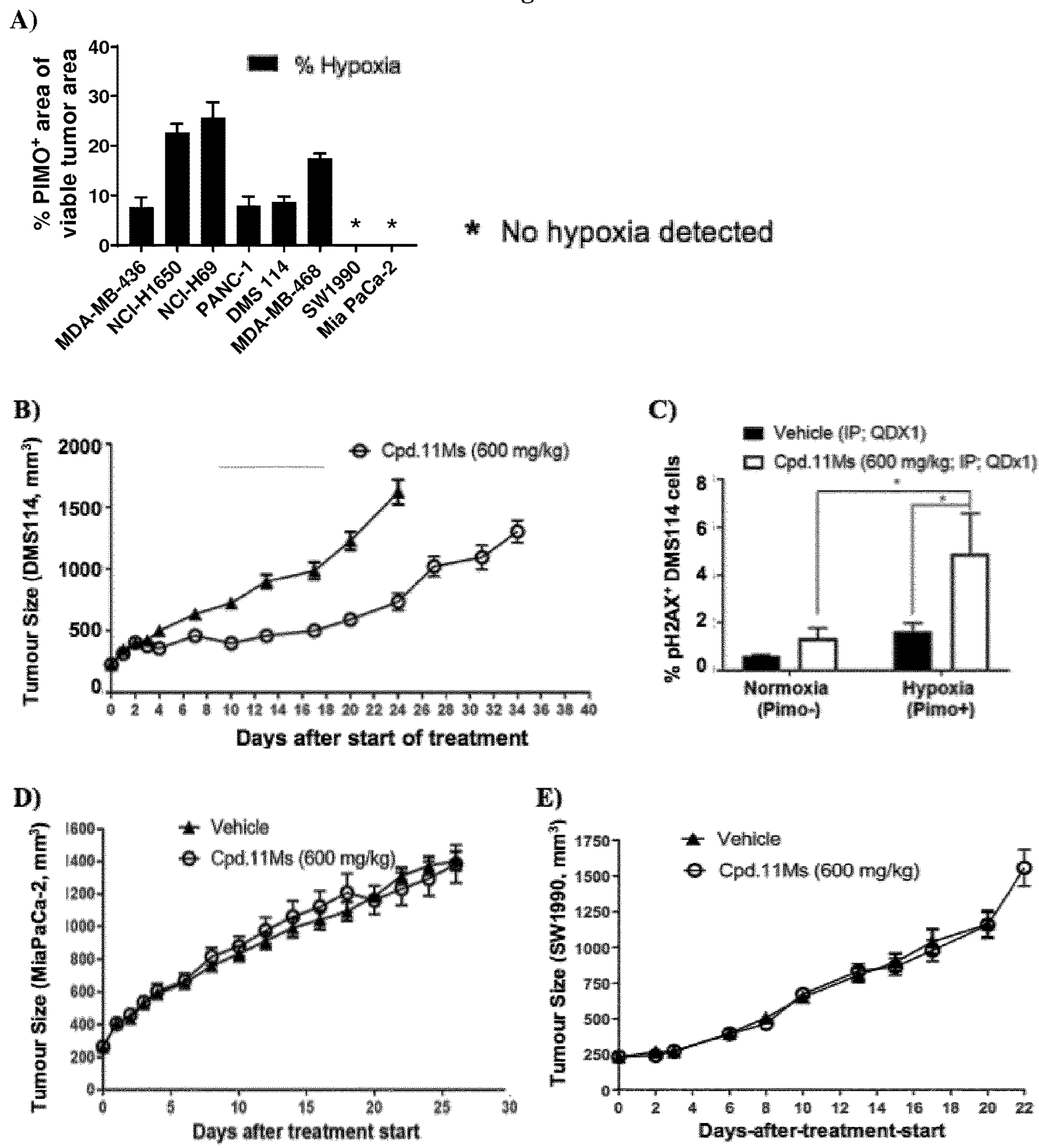
FIG. 7: efficacy of Cpd.11 Ms and relationship between cancer hypoxic state and biological activities of Cpd.11 Ms that are relevant for cancer cell-specific cytotoxicity. The hypoxic fraction in a panel of tumor xenografts generated from human cancer cell lines has been assessed using pimonidazole (PIMO+) staining. Two pancreatic tumor xenograft models did not show hypoxic areas (A). The antitumor efficacy of Cpd.11 Ms in the human cancer lung model DMS114 (B) has been established and DNA damage as assessed by pH2AX staining was mostly detected in the hypoxic areas as assessed by pimonidazole staining within the corresponding tumor xenograft (C). This antitumor effect of Cpd.11 Ms is not observed in the MiaPaca-2 (D) and SW1990 (E) xenografts from pancreatic cancer model in which hypoxia is not detected, even though these cell lines were shown to be highly Cpd.11 Ms-sensitive in anoxic conditions that are established using in vitro, cell culture model. DO is 28 days after tumor inoculation in DMS114 model, 14 days in SW1990 model, and 16 days in MiaPaCa-2 model.

The main conclusions is that, independently from type of cancer or sensitivity to a common drug such as cisplatin, the hypoxic status is associated to at least measurable anti-tumor regression, while pancreatic tumor xenograft models that did not show hypoxic areas (possibly due to inherent variability from experiment to experiment and specific location of tumor inoculation) appear also insensitive to Cpd.11 Ms cytotoxic activity. These hypoxic regions that appear specifically targeted by Cpd.11 Ms are also those presenting a concentration of DNA damages and adducts, possibly explaining the cytotoxicity of the compound (FIG. 7). A significantly higher DNA damage was observed in the Cpd.11 Ms treated animals when comparing normoxic (pimonidazole negative) with hypoxic (pimonidazole positive) areas (P=0.023), whereas no such statistically significant difference was noticed for the vehicle treated controls. In addition, a significant increase in DNA damage in the hypoxic (pimonidazole positive) areas was observed when comparing Cpd11Ms-treated animals with vehicle treated animals (P=0.038), while the differences in normoxic areas were not statistically significantly different. Therefore, these results further confirm the hypoxia-specific activation and consequent DNA damage. The clear impact of Cpd.11 Ms administration son hypoxia was also confirmed by pimonidazole immunohistochemical staining also in the MDA-MB-468[41] tumor xenograft model upon different treatment regimens (400-800 mg/kg from 1 to 5 consecutive days).

These data may be further validated in other animal models for the same Cpd.11 Ms and/or compared with data generated in the same models with other symmetrical and unsymmetrical haloalkanesulfonate mustards of Formula (I), alone or in combination with radiotherapy or compounds such as Erlotinib (a receptor tyrosine kinase inhibitor, which acts on the epidermal growth factor receptor and is used as drug to treat non-small cell lung cancer, pancreatic cancer and several other types of cancer), Doxorubcin (a chemotherapy medication used to treat several types of cancer such as breast cancer, bladder cancer, Kaposi's sarcoma or lymphoma), PD-1 inhibitors and PD-L1 inhibitors (a novel group of checkpoint inhibitors, mainly antibodies binding either of these proteins present on the surface of cells and Immune checkpoint inhibitors emerging as a front-line treatment for several types of cancer), PARP inhibitors (or other compound affecting the DNA repair in human cells), or Interleukin-2 (a cytokine active on cell-mediated immunity and used, in different recombinant forms, for treating cancers such as malignant melanoma or renal cell cancer). The combined administration of symmetrical and unsymmetrical haloalkanesulfonate mustards of Formula (I) such as Cpd.11 Ms, either simultaneous or sequential, with any of these compounds (or compounds falling in the same category of drugs) may improve the therapeutic response in cancer presenting hypoxic features according to one or more criteria such as synergism, reduction or dose and/or frequency of administration, broader therapeutic window, overcoming (or avoiding) resistance, improved cancer-specific immunological response, and/or reducing undesired side effects.

Example 4: Clinical Validation of Cpd.11 Ms as an Anti-Cancer Agent

Previous Examples 2 and 3 have presented preclinical biological and therapeutically relevant data generated with compound of Formula (I) such as Cpd.11 Ms and of Formula (II) such as Cpd.11c and Cpd.11d that support the evaluation of such compounds (and in particular of Cpd.11 Ms) as an anti-neoplastic agent in humans with solid tumors, in particular when the tumor is characterized as presenting hypoxic regions. Together with pharmacokinetics, pharmacology and toxicology of Cpd.11 Ms (and its metabolites), these data from the pre-clinical studies using the haloalkanesulfonate mustards of Formula (I) Cpd.11 Ms can be used to establish the clinical validation in clinical settings for treating cancer patients and specific cancer types. In particular the choice of subjects and clinical conditions in which a compound such as Cpd.11 Ms would provide with most relevant efficacy can be based on the features of tumor microenvironment, and in particular the gradients of oxygen diffusion and consumption, leading to sub-regions of hypoxia in a large fraction of solid tumors. Tumor adaptation to this imbalance between oxygen supply and demand is associated with poor clinical prognosis and similar hypoxic features have been established as a strong adverse prognostic feature in multiple cancer types, including head & neck, lung, cervical, prostate, soft-tissue sarcomas, and brain tumors. In addition, hypoxia has been indicated as a negative factor in further large variety of solid tumors including but not limited to breast, ovarian and pancreatic cancer, but also in hematologic malignancies.

Hypoxia has pronounced effects not only on overall tumor biology but also on the responsiveness to therapy, such as the hypoxia-specific resistance to radiotherapy (caused by the lack of oxygen required to fixate the DNA damage inflicted by ionizing radiation), or to chemotherapy and immunotherapy through multiple biological mechanisms described in the literature (such as suppression of immune reactivity, induction of tumor angiogenesis, selection of genotypes favouring cancer survival induction of invasiveness and metastasis under hypoxia). As shown in pre-clinical models, a compound such as Cpd.11 Ms can inhibit or block such hypoxia-driven mechanisms and can be formulated and administered at relatively high concentrations, with in vivo toxicology and pharmacokinetic properties that allow high exposure to the prodrug to enable its activation at therapeutically relevant levels in hypoxic sites. A compound such as Cpd.11 Ms can provide patients with direct (or indirect) therapeutic effects against cancer, in particular in conditions or patients where a drug counteracting the negative impact of hypoxia on other, standard-of-care treatment outcome is needed and it can be safely administered as a prodrug that is selectively activated in hypoxic tumor regions, with redistribution of the activated metabolites to nearby cells (bystander effect).

The effective clinical use and administration of haloalkanesulfonates mustards of Formula (I) such as Cpd.11 Ms can be associated to means for patient selection or stratification (based on hypoxia and/or sensitivity to the alkylating pharmacophore) which can be those generally available or specifically developed for these compounds (including liquid biopsy (blood)-based gene signature for CP-506). In order to evaluate the feasibility of clinical use and administration of haloalkanesulfonates mustards of Formula (I) such as Cpd.11 Ms, a comparison with other hypoxia-activated prodrugs (HAPs) such as evofosfamide (TH-302) and PR-104 can be made. Among these technologies, oxygen-enhanced and dynamic contrast-enhanced magnetic resonance imaging (OE-MRI and DCE-MRI), Positron emission tomography (PET), and other radiology-based approaches are technologies applicable in various cancer types that would allow detecting and quantifying tumor hypoxia content in patients in a non-invasive manner, thereby enabling patient stratification or patient selection. Furthermore, applying these radiomics-based or imaging technologies, with or without tracers, to follow-up the evolution of tumors during treatment (in terms of oxygenation and/or necrosis) may help establishing optimal timing of repeated cycles of treatments at standard or increasing doses of Cpd.11 Ms. Clinical imaging of hypoxia that can be applied to define preferred drug regimens, patients, clinical stages, and/or cancer sub-type have been reviewed in several recent publications (Challapalli A et al., 2017; Crispin-Ortuzar M et al., 2018; Liu J N et al., 2017; Pujara A C et al., 2019; Salem A et al., 2018).

Alternatively, or in addition to non-invasive technologies, tumor biopsies can be obtained from patients prior to and during the treatment period with Cpd.11 Ms to be analysed for determining tumor oxygenation and necrosis and other purposes such as proof-of-concept for Cpd.11 Ms activity and localization (to quantify the presence of Cpd.11c or Cpd.11d metabolites or specific DNA adducts and the induction of DNA damage in the tumor). Moreover, the a posteriori cancer characterization among tumors in one or more patients treated with Cpd.11 Ms may help defining which feature would predict cancer sensitivity to Cpd.11 Ms, e.g. by assessing hypoxia gene signatures or homologous recombination & DNA repair mechanism status in a given tumor, as described in the literature (Oda K et al., 2017; Sunada S et al., 2018; Sztupinszki Z et al., 2018; Talens F et al., 2017; von Wahlde M K et al., 2017; Yang L and West C M, 2018) or by using already commercialized test such as BRCA-related or HRD-related ones covering specific gene mutations (such as those commercialized by Myriad Genetics Inc., Utah USA). These partially overlapping purposes can also support the development of Cpd.11 Ms-specific gene signatures using liquid biopsies by allowing the correlation of the results obtained using two different types of samples and/or technologies. The availability of tumor biopsies will allow us to confirm clinically the feasibility to use liquid biopsies to detect any signature that is predictive of (lack of) Cpd.11 Ms therapeutic efficacy in individual patients and supports overall clinical development of Cpd.11 Ms in or more cancer (sub-) types.

Preliminary toxicology studies of the intravenous administration of Cpd.11 Ms in rats and dogs according to a dosing regimen consisting of 3 consecutive days of administration in a 3 weekly cycle (QDx3/cycle) have shown that potential haematological toxicity in tissues such as the bone marrow, the thymus and lymph nodes (known to have hypoxic niches) can be minimized at dosages at or below 400 mg/kg in the rat and at or below 100 mg/kg in the dog. As such, these levels correspond to 2360 $mg/m^2$ and 2000 $mg/m^2$, respectively, in human subjects. The efficacy studies in murine models that have typically used 600 mg/kg (which corresponds to 1800 $mg/m^2$ in humans) as a single cycle of 3 (QDx3) or 5 (QDx5) consecutive days showed high potency against cancer, and this was further pronounced on repeated cycles. Alternative dosing regimens also include weekly administration for up to 3 or 4 consecutive times of each 3 or 4 weekly cycle. In addition, also an initial dose of QDx3 or QDx5 could be combined with less frequent administration schedules that may still allow a therapeutic effect over tumor growth and development, such as up to 3 or 4 weekly dosages in 3 to 4 weekly cycles, or once a month (or every three-four weeks) schedules that be applied with or without the parallel treatment with the appropriate standard-of-care protocols.

The dose levels at which haloalkanesulfonates mustards of Formula (I) such as Cpd.11 Ms can be administered with minimal toxicities and high therapeutic efficacy is comprised in a range between 1200 and 2400 $mg/m^2$ (corresponding to 400-800 mg/kg in mouse). Such dosages and higher (up to 8000 $mg/m^2$) are expected to be well tolerated by the patient in monotherapy. Lower dosages (up to 4000 $mg/m^2$) may be required in combination settings, for example with conventional chemotherapies or radiotherapy, to ensure patient safety, but those are still expected to have therapeutic efficacy. These standard-of-care, therapeutic approaches target strongly proliferating cells and very often have cell cycle dependent activity. However, hypoxic regions of tumors typically harbor much fewer proliferating cells in view of the lack of nutrient and oxygen, and such tumor cells are typically much more resistant to many chemotherapies. Furthermore, the pre-clinical models have shown that haloalkanesulfonates mustards of Formula (I) such as Cpd.11 Ms can be highly cytotoxic against specific cancer cell lines that are resistant to cisplatin and/or chlorambucil. Thus, by virtue of its nature and biological effects (i.e. hypoxia selective activation and highly potent alkylating activity), haloalkanesulfonates mustards of Formula (I) such as Cpd.11 Ms present a very different therapeutic moiety, in particular when compared to other alkylating agents, that can be exploited in both cancer monotherapy and but more preferably in cancer combination regimens that involve standard-of-care treatments such as chemotherapy, inducing a better response, increasing the progression-free survival rate, quality of life, and ultimately the overall survival in those patients.

This pre-clinical development and validation phase of haloalkanesulfonates mustards of Formula (I) such as Cpd.11 Ms has allowed defining specific preferred drug preparations that can be manufactured in GMP conditions compatible for clinical validation investigation, for example as a powder filled vial that is sterilized under gamma irradiation. Cpd.11 Ms is sufficiently stable to such sterilizing conditions and also sufficiently water-soluble to immediately prepare a dilution in water for injection at 100 mg/mL for addition to a dextrose infusion bag. NaOAc can be added to ensure that the pH is acceptable for intravenous administration. The findings obtained during pre-clinical validation and toxicology of haloalkanesulfonates mustards of Formula (I) such as Cpd.11 Ms can be used as basis for designing clinical studies in selected, small patient populations, and then used for establishing larger clinical studies in which the inclusion criteria and profile of patients is further defined to better characterize the patient population who would benefit the most of such anti-cancer therapies. Indeed, hypoxia is correlated with tumor aggressiveness or malignancy and is known to induce resistance to standard-of-care therapies, rather than driving proliferation and tumour growth, thus haloalkanesulfonates mustards of Formula (I) such as Cpd.11 Ms may be combined with other treatments targeting well oxygenated-proliferating cells in order to maximize its efficacy.

A preliminary trial may be designed as a Phase I/II study, open-label, uncontrolled, multi-center, multiple dose-escalation study of Cpd.11 Ms. The initial portion of the study (Phase Ia part) will be a dose escalation study in monotherapy in patients with any solid tumor who have exhausted all existing treatment options. In order to define the maximum tolerated dose (MTD) and pharmacokinetic profile, an initial 3+3 subject per dose cohort design can be used, wherein each patients receive the starting dose of Cpd.11 Ms via intravenous infusion over 2 hours for three consecutive days, followed by a 18-day observation period (QDx3 regimen, every 3 wks). As this is a first in human study, the first patient of each cohort is treated and followed up for a week before the next 2 patients are recruited in order to prevent any safety issue. Once the three patients have finished their cycles, a meeting will be held with clinical investigators to assess the safety and tolerability of the treatment. If no dose limiting toxicities (DLTs) are observed, then the next dose level will be evaluated, expanding up to 24 patients. If 1 out of 3 subjects experiences a DLT, then the cohort will be expanded to 6 subjects. If 2 or more out of 3 subjects, or 2 or more out of 6 subjects experience a DLT in a dose cohort, then this dose level will be deemed to be not tolerated, with the MTD being defined as the highest dose level that causes ≤1 of 6 patients to experience DLT in the first cycle. The dose escalation will occur with decreasing increments according to a modified Fibonacci sequence in the serial cohorts, each patient receiving the assigned dose of Cpd.11 Ms every 21 days as long as deemed beneficial for the patient by the investigator.

Once the third cohort of the Phase Ia part has been evaluated as well tolerated, a Phase Ib part can be started up to run in parallel with the Phase Ia. This second part can also be a dose escalation design but in a combination setting, in particular with platinum-etoposide (with or without anti-PD1 or anti-PD-L1), including up to 15 patients under QDx3 regimen (repeated every three weeks). The safety and tolerability of Cpd.11 Ms in combination with platinum-etoposide can be evaluated as first or second line treatment in patients with small cell lung cancer (SCLC), which remains one of the most aggressive types of cancer, with 5-year survival rates below 5%. Multiple studies have highlighted the presence of hypoxia in SCLC tumours, and it is very high unmet need, both in treatment naïve patients and those with relapsed/refractory disease, with no change in standard-of-care for over 30 years, apart from the recent FDA approval of anti-PD-L1 in combination with platinum-etoposide in ES-SCLC. First line SCLC treatment very much remains platinum-etoposide chemotherapy and less toxic treatments that postpone disease progression and/or increase health-related quality of life parameters are still highly needed, SCLC being an orphan disease (ORPHA 70573) which means a faster and dedicated track to drug approval.

The administration of Cpd.11 Ms may be most valuable in patient populations that are known to have a high recurrence rate due to the incomplete targeting and/or rise of resistance upon repeated treatment. The 3+3 clinical design as defined above can be used to determine the recommended phase II dose (RP2D) that may be then used for treating an expansion cohort (including up to 50 patients under a QDx3 regimen repeated every three weeks) to further assess the tolerability and safety of the combination and perform a preliminary efficacy assessment by tumor regression with a corresponding longer time of remission, progression free survival, and overall survival. A similar clinical development program is envisaged for pancreatic cancer (in combination with gemcitabine +/−n-abraxane), triple negative breast cancer (in combination with n-abraxane) and NSCLC (in combination with anti-PD1 or anti-PD-L1 therapy).

During the Phase Ia/Ib, and Phase II studies and or in later, larger randomised studies, the evaluation and comparison of therapeutically relevant read-out can be combined with the evaluation of surrogate end-points, biomarkers, drug metabolites, and other biological features that can be investigated by using existing technologies into patients and clinical samples and guide the choice of regimens, dosages, and/or combinations more adapted to a given patient population and cancer type or stage. On the basis of these clinical and biological findings, other potential settings for combinatorial use of Cpd.11 Ms or other haloalkanesulfonate mustards of Formula (I) can be evaluated in clinical settings with different and broader patient populations that presently receive standard-of-care treatments compatible with Cpd.11 Ms administration dosages and regimens, in order to confirm clinical feasibility and expected efficacy. Examples of such cancers in which Cpd.11 Ms can provide with therapeutically relevant effects, as already in part validated in some animal models, are triple negative breast cancer (TNBC; in combination with a taxane or an anthracycline, even further combined with cyclophosphamide or a PARP inhibitor), non-small cell lung cancer (NSCLC; in combination with cisplatin alone or also with taxane, gemcitabine, pemetrexed, etoposide, or a checkpoint inhibitor such as an anti-PD-1 or anti-PD-L1 antibody), small cell lung cancer (SCLC: in further combinations with a checkpoint inhibitor such as an anti-PD-1 or anti-PD-L1 antibody, a PARP inhibitor, carboplatin, lurbinectedin, irinotecan), Pancreatic ductal adenocarcinoma (PDAC; in combination with gemcitabine and abraxane, FOLFOX or FOLFINIROX), metastatic castration-resistance prostate cancer (mCRPC; in combination with docetaxel/carbazitaxel in addition to anti-androgenic drugs, a taxanes, platinum, abiraterone or enzalutamide), ovarian cancer (in combination with platinum, carboplatin, and/or a PARP inhibitor). In addition, such regimens may also include radiotherapy.

Additional standard-of-care treatment that can be investigated in combination with Cpd.11 Ms or other haloalkanesulfonate mustards of Formula (I) that may require further studies in animal models are radiotherapy (for localized or locally invasive treatment, e.g. in NSCLC or prostate cancer), or as neoadjuvant before surgery (e.g. for mCRPC). If efficacy is confirmed, this approach can open the wide range of indications in human cancers for clinical development, also by anticipating and adapting the Cpd.11 Ms or other haloalkanesulfonate mustards of Formula (I) at earlier stages of cancer that are listed above or other ones such as ones previously listed as Cpd.11 Ms-sensitive given the presence of hypoxic regions (such as gastrointestinal cancer, prostate cancer, ovarian cancer, brain cancer, head and neck cancer, or soft-tissue sarcoma). In such settings, the therapeutic strategy and drug regimens can be adapted in view of biological features of specific cancers and/patients that can be measured before and during treatment (e.g. in blood samples or in tumor biopsies).

REFERENCES

Baran N and Konopleva M, Clin Cancer Res. 2017, 23:2382-2390.
Cai Z et al., Mol Biosyst. 2015, 11:791-800.
Challapalli A et al., 2017. Clin Transl Imaging 5 (3): 225-253.
Crispin-Ortuzar M et al., 2018. Radiother Oncol, 127 (1): 36-42.
Dai X et al., J Cancer. 2017. 8:3131-3141.
Deer E L et al., Pancreas. 2010, 39:425-35.
Dhingra V K, et al., Indian J Radiol Imaging. 2015, 25:332-41.
Fan G et al., J Hematol Oncol. 2015, 8:130
Hunter F et al., Mol Cancer Ther. 2014. 13:2501-14.
Hunter F et al., Br J Cancer 2016, 114 1071-7.
Liu J N et al., 2017. Chem Rev, 117 (9): 6160-6224.
Meng F et al., Mol Cancer Ther. 2012, 11:740-51.
Menyhárt O et al., Biochim Biophys Acta. 2016, 1866:300-319.
Mirabello V et al., Front Chem. 2018 Feb. 23; 6:27.
Mistry I N et al., Int J Radiat Oncol Biol Phys. 2017, 98:1183-1196.
Oda K et al., Int J Clin Oncol. 2017 August; 22 (4): 611-618.
Papkovsky DB and Dmitriev R I, Cell Mol Life Sci. 2018 75 (16): 2963-2980
Phillips R, Cancer Chemother Pharmacol. 2016, 77:441-457.
Pujara A C et al., 2019. J Magn Reson Imaging, 9 (2): 328-342.
Salem A et al., 2018 J Natl Cancer Inst, 2018; 110 (1).
Silva V L and Al-Jamal W T, J Control Release. 2017, 253:82-96.
Sliwkowski & Mellman, Science. 2013, 341:192-8
Stornetta A et al., Biochem Pharmacol. 2018. 154:64-74.
Sunada S et al., Cancer Sci. 2018; 109 (4): 893-899.
Sztupinszki Z et al., NPJ Breast Cancer. 2018; 4:16.
Talens F et al., Expert Opin Drug Discov. 2017; 12 (6): 565-581.
Tiller K and Tessier P, Annu Rev Biomed Eng. 2015, 17:191-216.
von Wahlde M K et al., Clin Cancer Res. 2017; 23 (5): 1193-1199.
Yang L and West C M, Br J Radiol. 2018: 20180036.
Weiner G. Nat Rev Cancer. 2015, 15:361-370.
Wilson W R et al., Cancer Res. 2002, 62:1425-1432.

The invention claimed is:

1. A method for the treatment of a solid, metastatic cancer affecting a Human patient, wherein said solid cancer is selected from a group consisting of breast cancer and pancreatic cancer, comprising a step of administering an effective amount of 2-((2-bromoethyl) (5-(4-ethylpiperazine-1-carbonyl)-2-(methylsulfonyl)-4-nitrophenyl)amino) ethyl methanesulfonate or a pharmaceutically acceptable salt, solvate, or stereoisomer of said compound, wherein presence of a hypoxia gene expression signature has been assessed and confirmed in said solid metastatic cancer, and wherein said patient has previously been treated with a radiotherapy, chemotherapy, and/or an immunotherapy.

2. The method of claim 1, wherein the compound is administered to said Human patient who has been previously treated with a compound selected from a group consisting of carboplatin, cisplatin, miboplatin, nedaplatin or oxaliplatin.

3. The method of claim 1, wherein the compound prevents drug resistance, immunological escape, relapse, or metastasis of said cancer in said Human patient.

4. The method of claim 1, wherein the compound is formulated for parenteral, intratumoral, trans-arterial embolization, or oral administration.

5. The method of claim 1, wherein the compound is administered at a dose comprised between 40 and 10,000 $mg/m^2$.

6. The method of claim 1, wherein the compound is administered to said Human patient, simultaneously or sequentially, with another therapeutic agent or therapy.

7. The method of claim 6, wherein the other therapy is radiotherapy.

8. The method of claim 6, wherein the other therapy is chemotherapy.

9. The method of claim 1, wherein the hypoxia gene expression signature is assessed using pimonidazole (PIMO+) staining or an equivalent assessment.

10. The method of claim 1, wherein the chemotherapy is cisplatin.

11. The method of claim 8, wherein the chemotherapy is selected from cisplatin, carboplatin, paclitaxel, gemcitabine, docetaxel, doxorubicin, gemcitabine: nab-paclitaxel.

12. The method of claim 1, wherein said solid cancer is triple negative breast cancer or pancreatic ductal adenocarcinoma.

13. A method for the treatment of a solid, metastatic cancer affecting a Human patient comprising:
- selecting said solid metastatic cancer from a group consisting of breast cancer and pancreatic cancer;
- assessing a homologous recombination and DNA repair mechanism status of said solid cancer and confirming said solid cancer has a hypoxia gene expression signature; and
- administering an effective amount of 2-((2-bromoethyl) (5-(4-ethylpiperazine-1-carbonyl)-2-(methylsulfonyl)-4-nitrophenyl)amino)ethyl methanesulfonate or a pharmaceutically acceptable solvate, or stereoisomer thereof in said cancer.

14. The method of claim 13, wherein said hypoxia gene signature has been confirmed for said solid cancer using pimonidazole (PIMO+) staining or an equivalent assessment.

15. The method of claim 13, wherein the compound is administered to said Human patient, simultaneously or sequentially, with another therapeutic agent or therapy.

16. The method of claim 15, wherein the other therapy is selected from cisplatin, carboplatin, paclitaxel, gemcitabine, docetaxel, doxorubicin, gemcitabine or nab-paclitaxel.

17. The method of claim 16, wherein the said 2-((2-bromoethyl) (5-(4-ethylpiperazine-1-carbonyl)-2-(methylsulfonyl)-4-nitrophenyl)amino)ethyl methanesulfonate or a pharmaceutically acceptable solvate, or stereoisomer thereof is administered in a combination therapy with radiotherapy.

18. The method of claim 15, wherein the said 2-((2-bromoethyl) (5-(4-ethylpiperazine-1-carbonyl)-2-(methylsulfonyl)-4-nitrophenyl)amino)ethyl methanesulfonate or a pharmaceutically acceptable solvate, or stereoisomer thereof is administered in a combination therapy with another compound selected from carboplatin, cisplatin, miboplatin, nedaplatin or oxaliplatin.

* * * * *